United States Patent
Ludlow et al.

(10) Patent No.: US 8,388,561 B2
(45) Date of Patent: Mar. 5, 2013

(54) SYSTEMS AND METHODS FOR RECOVERY FROM MOTOR CONTROL VIA STIMULATION TO A SUBSTITUTED SITE TO AN AFFECTED AREA

(75) Inventors: Christy Ludlow, Bethesda, MD (US); Newlin Morgan, Bethesda, MD (US); George Dold, Boyds, MD (US); Soren Lowell, Syracuse, NY (US); Katie Dietrich-Burns, Fort Howard, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 1042 days.

(21) Appl. No.: 12/211,633

(22) Filed: Sep. 16, 2008

(65) Prior Publication Data
US 2009/0187124 A1    Jul. 23, 2009

(51) Int. Cl.
*A61H 1/00*    (2006.01)
(52) U.S. Cl. ........ 601/48; 601/46; 601/84; 601/DIG. 15
(58) Field of Classification Search ............... 601/46, 601/48, 49, 69, 70, 71, 78, 79, 84, 87, DIG. 15
See application file for complete search history.

(56) References Cited

U.S. PATENT DOCUMENTS

| | | | |
|---|---|---|---|
| 4,143,648 A | 3/1979 | Cohen et al. | |
| 4,685,448 A | 8/1987 | Shames et al. | |
| 5,086,788 A | 2/1992 | Castel et al. | |
| 5,111,814 A | 5/1992 | Goldfarb | |
| 5,350,407 A | 9/1994 | McClure et al. | |
| 5,562,718 A | 10/1996 | Palermo | |
| 5,725,564 A | 3/1998 | Freed et al. | |
| 5,871,808 A | 2/1999 | Thompson et al. | |
| 5,891,185 A | 4/1999 | Freed et al. | |
| 5,897,579 A | 4/1999 | Sanders | |

(Continued)

FOREIGN PATENT DOCUMENTS

| CN | 101716394 | 6/2010 |
|---|---|---|
| EP | 0 226 333 A1 | 6/1987 |

(Continued)

OTHER PUBLICATIONS

International Preliminary Report on Patentability and Written Opinion of the International Searching Authority for International Application No. PCT/US2006/025535 issued on Jan. 9, 2008.

(Continued)

*Primary Examiner* — Quang D Thanh
(74) *Attorney, Agent, or Firm* — Knobbe Martens Olson & Bear LLP

(57) ABSTRACT

A device and methods for treating a subject with dysphagia or other neurological disease, neurological disorder, neurological injury, neurological impairment or neurodegenerative disease that affects voluntary motor control of the hyoid, pharynx, larynx, or oropharyngeal area is disclosed. A device of the invention generally comprises a vibrotactile stimulator for applying at least one stimulus to the outside surface of a subject's neck; a connector for attaching the vibrotactile stimulator to an outside surface of the subject's neck, and a switch control communicatively connected to the vibrotactile stimulator to selectively engage a manual stimulation module and/or automatic stimulation module. Stimulation of an outside surface of the throat area of a subject by a device of the invention stimulates a swallowing reflex in the subject.

36 Claims, 23 Drawing Sheets

U.S. PATENT DOCUMENTS

| | | | |
|---|---|---|---|
| 5,987,359 | A | 11/1999 | Freed et al. |
| 6,039,679 | A | 3/2000 | Yu |
| 6,104,958 | A | 8/2000 | Freed et al. |
| 6,131,535 | A | 10/2000 | So |
| 6,198,970 | B1 | 3/2001 | Freed et al. |
| 6,343,232 | B1 | 1/2002 | Mower |
| 6,354,991 | B1 | 3/2002 | Gross et al. |
| 6,393,323 | B1 | 5/2002 | Sawan et al. |
| 6,735,315 | B1 | 5/2004 | Ifukube et al. |
| 7,039,468 | B2 | 5/2006 | Freed et al. |
| 7,182,738 | B2* | 2/2007 | Bonutti et al. ............... 601/5 |
| 7,280,873 | B2 | 10/2007 | Freed et al. |
| 7,349,739 | B2 | 3/2008 | Harry et al. |
| 7,606,623 | B2 | 10/2009 | Ludlow et al. |
| 7,660,636 | B2 | 2/2010 | Castel et al. |
| 2002/0010495 | A1 | 1/2002 | Freed et al. |
| 2002/0049479 | A1 | 4/2002 | Pitts |
| 2002/0133194 | A1 | 9/2002 | Leelamanit et al. |
| 2003/0093128 | A1 | 5/2003 | Freed et al. |
| 2004/0133133 | A1* | 7/2004 | Dreimann et al. ............ 601/15 |
| 2005/0049453 | A1 | 3/2005 | Faulkner |
| 2005/0049856 | A1 | 3/2005 | Baraff |
| 2006/0030794 | A1 | 2/2006 | Nation et al. |
| 2007/0073361 | A1 | 3/2007 | Goren et al. |
| 2007/0293926 | A1 | 12/2007 | Dunlay et al. |
| 2008/0077192 | A1 | 3/2008 | Harry et al. |
| 2009/0048645 | A1 | 2/2009 | Philipp et al. |
| 2009/0054980 | A1 | 2/2009 | Ludlow et al. |
| 2010/0016908 | A1 | 1/2010 | Martin et al. |
| 2010/0049103 | A1 | 2/2010 | Ludlow et al. |
| 2011/0125212 | A1 | 5/2011 | Tyler |

FOREIGN PATENT DOCUMENTS

| | | | |
|---|---|---|---|
| JP | 11-500339 | | 1/1999 |
| JP | 2006-500994 | | 1/2006 |
| JP | 2007-151736 | | 6/2007 |
| WO | WO 92/21407 | | 12/1992 |
| WO | WO 97/15349 | | 5/1997 |
| WO | WO 2004/028433 | A2 | 4/2004 |
| WO | WO 2007/005582 | | 1/2007 |
| WO | WO 2007/123746 | | 11/2007 |
| WO | WO 2007123746 | * | 11/2007 |

OTHER PUBLICATIONS

International Search Report and Written Opinion of the International Searching Authority for International Application No. PCT/US2007/007993 mailed on Mar. 5, 2008.

International Preliminary Report on Patentability and Written Opinion of the International Searching Authority for International Application No. PCT/US2007/007993 issued on Sep. 30, 2008.

International Search Report for International Application No. PCT/US2009/057158 mailed on Mar. 26, 2010.

International Preliminary Report on Patentability and Written Opinion of the International Seaching Authority for International Application No. PCT/US2009/057158 issued on Mar. 22, 2011.

Office Action issued in Australian Patent Application No. 2006265985 on Oct. 20, 2009.

Notice of Acceptance issued in Australian Patent Application No. 2006265985 on Dec. 1, 2010.

Office Action issued in European Patent Application No. 06785933.0 on Feb. 10, 2011.

Restriction Requirement issued in U.S. Appl. No. 12/240,398 on Nov. 23, 2011.

Extended European Search Report for European Patent Application No. 11005014.3 dated Sep. 30, 2011.

Office Action issued in Japanese Patent Application No. 2008-520302 on Nov. 15, 2011.

Experia™: The Next Generation of VitalStim® Therapy brochure, 2007 Encore Medical, L.P. and Affiliates, 2 pages.

Office Action issued in Australian Patent Application No. 2011201177, dated Feb. 23, 2012.

Office Action issued in U.S. Appl. No. 11/993,094 dated Mar. 13, 2012.

Office Action issued in U.S. Appl. No. 12/240,398, dated Dec. 28, 2011.

Office Action issued in EP Application No. 11 005 014.3, dated Jun. 8, 2012.

Office Action in Australian Patent Application No. 2011201177, dated Aug. 1, 2012.

Final Office Action issued in U.S. Appl. No. 12/240,398, dated Jun. 21, 2012.

Restriction Requirement issued in U.S. Appl. No. 11/993,094 on Jan. 24, 2012.

Aviv et al., "Laryngopharyngeal sensory testing with modified barium swallow as predictors of aspiration pneumonia after stroke", *Laryngoscope*, 107:1254-1260 (1997).

Aviv et al., "Silent laryngopharyngeal sensory deficits after stroke", *Ann Otol Rhinol. Laryngol.*, 106:87-93 (1997).

Aviv et al., "Supraglottic and pharyngeal sensory abnormalities in stroke patients with dysphagia", *Ann Otol Rhinol.Laryngol.*, 105:92-97 (1996).

Bara-Jimenez et al., "Abnormal somatosensory homunculus in dystonia of the hand", *Ann Neurol.*, 44(5):828-831 (1998).

Bara-Jimenez et al., "Sensory discrimination capabilities in patients with focal hand dystonia", *Ann Neurol.*, 47(3):377-380 (2000).

Bidus et al., "Effects of Adductor Muscle Stimulation on Speech in Abductor Spasmodic Cysphonia", *The Laryngoscope*, 110:1943-1949 (2000).

Bielamowicz et al., "Effects of botulinum toxin on pathophysiology in spasmodic dysphonia", *Ann Otol Rhinol Laryngol*, 109:194-203 (2000).

Burnett et al., "Laryngeal elevation achieved by neuromuscular stimulation at rest", *J Appl Physiol*, 94(1):128-134 (2003).

Burnett et al., "Self-Triggered Functional Electrical Stimulation During Swallowing", *J Neurophysiol*, 94(6):4011-4018 (2005).

Conforto et al. "Increase in hand muscle strength of stroke patients after somatosensory stimulation", *Ann Neurol*, 51(1):122-125 (2002).

Supplementary European Search Report dated May 14, 2008.

Daly et al., "Performance of an intramuscular electrode during functional neuromuscular stimulation for gait training post stroke", *Journal of Rehabilitation Research and Development*, 38(5):513-526 (2001).

de Larminat et al., "Alteration in swallowing reflex after extubation in intensive care unit patients", *Crit Care Med*, 23(3):486-490 (1995).

de Nil et al., "Kinaesthetic acuity of stutterers and non-stutterers for oral and non-oral movements", *Brain*, 1 14:2145-2158 (1991).

Dick et al., "Interaction between central pattern generators for breathing and swallowing in the cat", *J Physiol*, 465:715-730 (1993).

Folstein et al., "Mini-mental state. A practical method for grading the cognitive state of patients for the clinician", *J Psychiatr Res*, 12(3):189-198 (1975).

Fraser et al., "Differential changes in human pharyngoesophageal motor excitability induced by swallowing, pharyngeal stimulation, and anesthesia", *Am J Physiol Gastrointest Liver Physiol*, 285(1):G137-144 (2003).

Freed et al., "Electrical Stimulation for Swallowing Disorders Caused by Stroke", *Respiratory Care*, 46(5):466-474 (2001).

Hägg et al., "Effects of motor and sensory stimulation in stroke patients with long-lasting dysphagia", *Dysphagia*, 19:219-230 (2004).

Hamdy et al., "Modulation of human swallowing behaviour by thermal and chemical stimulation in health and after brain injury", *Neurogastroenterol Motil*, 15(1):69-77 (2003).

Handa et al., "Development of Percutaneous Intramuscular Electrode for Multichannel FES System", *IEEE Transactions on Biomedical Engineering*, 36(7):705-710, (1989).

Haslinger et al., "Silent event-related fMRI reveals reduced sensorimotor activation in laryngeal dystonia", *Neurology*, 65:1562-1569 (2005).

Hrycyshyn et al., "Electromyography of the Oral Stage of Swallowing in Man", *Am. J. Anat.*, 133:333-340 (1972).

Humbert et al., "The effect of surface electrical stimulation on hyolaryngeal movement in normal individuals at rest and during swallowing", *J Appl Physiol*, 101:1657-1663 (2006).

Humbert et al., "The Effect of Surface Electrical Stimulation on Vocal Fold Position", *Laryngoscope*, 118:14-19 (2007).
International Search Report dated Apr. 9, 2004 (PCT/US03/30032).
International Search Report dated Nov. 21, 2006 (PCT/US2006/025535).
Jafari et al., "Sensory regulation of swallowing and airway protection: a role for the internal superior laryngeal nerve in humans", *J Physiol*, 550(Pt I):287-304 (2003).
Jean, "Control of the central swallowing program by inputs from the peripheral receptors. A review", *J Auton, Ner. Syst.*, 10:225-233 (1984).
Leelamanit et al., "Synchronized electrical stimulation in treating pharyngeal dyspagia", *Laryngoscope*, 112(12):2204-2210 (2002).
Logemann et al., "Effects of a sour bolus on oropharyngeal swallowing measures in patients with neurogenic dysphagia", *J Speech Hear Res*, 38(3):556-563 (1995).
Logemann, "Noninvasive approaches to deglutitive aspiration", *Dysphagia*, 8(4):331-333 (1993).
Loucks et al., "Laryngeal muscle responses to mechanical displacement of the thyroid cartilage in humans", *J Appl Physiol*, 99(3):922-930 (2005).
Lowell et al., "Sensory stimulation activates both motor and sensory components of the swallowing system", *NeuroImage*, 42:285-295 (2008).
Ludlow et al., "Chronic Intermittent Stimulation of the Thyroarytenoid Muscle Maintains Dynamic Control of Glottal Adduction", *Muscle and Nerve*, 23:44-57 (2000).
Ludlow et al., "Dynamic aspects of phonatory control in spasmodic dysphonia", *J Speech Hear Res*, 30:197-206 (1987).
Ludlow et al., "Effects of Surface Electrical Stimulation Both at Rest and During Swallowing in Chronic Pharyngeal Dysphagia", *Dysphagia*, 22:1-10 (2007).
Ludlow et al., "Three-Dimensional Changes in the Upper Airway During Neuromuscular Stimulation of Laryngeal Muscles", *Journal of Artificial Organs*, 23:463-465 (1999).
Lundy et al., "Aspiration: Cause and Implications", *Otolaryngol Head Neck Surg.*, 120(4):474-478 (1999).
Marsolais et al., "Implantation techniques and experience with percutaneous intramuscular electrodes in the lower extremities", *J. Rehabil. Res. Dev.*, 23(3):1-8 (1986).
Mifflin, "Intensity and frequency dependence of laryngeal afferent inputs to respiratory hypoglossal motoneurons", *J Appl Physiol*, 83:1890-1899 (1997).
Mortimer et al., "Intramuscular Electrical Stimulation: Tissue Damage", *Ann. Biomed. Eng.*, 8:235-244 (1980).
Nishino et al., "Cough and other reflexes on irritation of airway mucosa in man", *Pulm Pharmacol*, 9(5-6):285-292 (1996).
Ootani et al., "Convergence of afferents from the SLN and GPN in cat medullary swallowing neurons", *Brain Res Bull*, 37(4):397-404 (1995).
Park et al., "A pilot exploratory study of oral electrical stimulation on swallow function following stroke: an innovative technique",*Dysphagia*, 12(3):161-166 (1997).

Peurala et al., "Cutaneous electrical stimulation may enhance sensorimotor recovery in chronic stroke", *Clin Rehabil.*, 709-716 (2002).
Pick et al., "Pulmonary aspiration in a long-term care setting: clinical and laboratory observations and an analysis of risk factors", *J Am Geriatr Soc*, 44(7):763-768 (1996).
Pommerenke, "A study of the sensory areas eliciting the swallowing reflex", *American Journal of Physiology*, 84(1):36-41 (1927).
Portone et al., "A review of patient adherence to the recommendations for voice therapy", *J. Voice*, 22:192-196 (2008).
Power et al., "Changes in pharyngeal corticobulbar excitability and swallowing behavior after oral stimulation", *Am J Physiol Gastrointest Liver Physiol*, 286(1):G45-50 (2004).
Power et al., "Evaluating oral stimulation as a treatment for Dysphagia after stroke", *Dysphagia*, 21(1):49-55 (2006).
Robbins et al., "Swallowing and dysphagia rehabilitation : translating principles of neural plasticity into clinically orientated evidence", *J Speech Lang. Hear. Res.*, 51:S276-300 (2008).
Scheiner et al., "Design and Clinical Application of a Double Helix Electrode for Functional Electrical Stimulation", *IEEE Transactions of Biomedical Engineering*, 41(5):425-431 (1994).
Sedory-Holzer et al., "The swallowing side effects of botulinum toxin type A injection in spasmodic dysphonia", *Laryngoscope*, 106:86-92 (1996).
Setzen et al., "The association between laryngopharyngeal sensory deficits, pharyngeal motor function, and the prevalence of aspiration with thin liquids", *Otolaryngol Head Neck Surg*, 128(1):99-102 (2003).
Spiro et al., "Activation and Coordination Patterns of the Suprahyoid Muscles During Swallowing", *Laryngoscope*, 104: 1376-1382 (1994).
Stanic et al., "Multichannel Electrical Stimulation for Correction of Hemiplegic Gait", *Scand J. Rehabil. Med.*, 10:75-92 (1978).
Strojnik et al., "Treatment of Drop Foot Using an Implantable Peroneal Underknee Stimulator", *Scand J. Rehabil. Med.*, 19:37-43 (1987).
Struppler et al., "Modulation of sensorimotor performances and cognition abilities induced by RPMS: clinical and experimental investigations", *Suppl Clin Neurophysiol.*, 56:358-367 (2003).
Sundgren et al., "Elevation of the larynx on normal and abnormal cineradiogram", *The British Journal of Radiology*, 66:768-772 (1993).
Theurer et al., "Oropharyngeal stimulation with air-pulse trains increases swallowing frequency in healthy adults", *Dysphagia*, 20(4):254-260 (2005).
van Dijk et al., "Effects of transcutaneous electrical nerve stimulation (TENS) on non-pain related cognitive and behavioural functioning", *Rev Neurosci.*, 13:257-270 (2002).
Waters et al., "Functional Electrical Stimulation of the Peroneal Nerve for Hemiplegia", *The Journal of Bone and Joint Surgery*, 67:792-793 (1985).
Final Office Action in Japanese Application No. 2008-520302, dated Aug. 14, 2012.

* cited by examiner t=3.33, p=.0025

SYSTEMS AND METHODS FOR RECOVERY FROM MOTOR CONTROL VIA STIMULATION TO A SUBSTITUTED SITE TO AN AFFECTED AREA

STATEMENT OF RIGHTS TO INVENTION MADE UNDER FEDERALLY SPONSORED RESEARCH AND DEVELOPMENT

The work performed during the development of this application utilized support from the National Institutes of Health. The United States government has certain rights in the invention.

INCORPORATION DATA

U.S. patent application Ser. No. 11/993,094, filed Dec. 19, 2007, PCT Patent App. No. PCT/US2006/025535, filed Jun. 30, 2006, U.S. Prov. Patent App. Ser. No. 60/695,424, filed Jul. 1, 2005, U.S. Prov. Patent App. Ser. No. 60/787,215, filed Mar. 30, 2006, and PCT Patent App. No. PCT/US2007/007993, filed Mar. 30, 2007, are all hereby incorporated by reference.

TECHNICAL FIELD

The present disclosure relates generally to systems and methods for treating and managing neurological disease comorbidities. More specifically, the present disclosure relates generally to systems and methods for treating and managing diseases and disorders affecting the muscles of the neck and/or pharynx.

BACKGROUND

A wide range of neurological diseases and disorders exist that are not well addressed by present medical technology. Among these, dysphagia (a swallowing disorder that affects the central nervous system thereby weakening neuromuscular control and effectively reducing the ability to properly swallow) is a particularly life threatening disorder placing persons at risk of aspiration pneumonia. Patients at risk of aspiration pneumonia have a 17% survival rate over three years (Pick et al., 1996). Estimates are that over 7 million persons in the U.S. have dysphagia as a result of neurological diseases or disorders such as stroke, traumatic brain injury, brain tumors, Parkinson's disease, multiple sclerosis (Humbert, Lynch and Ludlow, in preparation 2008) and other neurological diseases and over 300,000 persons develop a swallowing disorder as a result of a neurological disease or disorder in the United States each year. Over 50% of patients with neurological diseases or disorders are at risk of aspiration pneumonia because of loss of central nervous system control of their swallowing resulting in either delayed or reduced elevation of the hyolaryngeal complex, which does not allow them to prevent food or liquid from entering the airway (Lundy et al., 1999). Normally the hyoid and larynx are raised by about 20 mm during swallowing producing an inversion of the epiglottis and assisting with opening of the upper esophageal sphincter.

Frequently, patients having dysphagia require 24-hour attention to prevent aspiration and ensure that the passage of food and/or fluids, particularly saliva, into the respiratory system is minimized. It has previously been shown that glass rod pressure stimulation to the faucial pillars in the mouth can trigger swallowing (Pommerenke, 1927) while chemical blocks of laryngeal sensation severely impair volitional swallowing in normal adults (Jafari, Prince, Kim, & Paydarfar, 2003). Pharyngeal stimulation can initiate laryngeal closure and elevation for swallowing in animals (Jean, 1984), while laryngeal stimulation will trigger a swallow (Nishino, Tagaito, & Isono, 1996). In humans, when sensory stimulation of the oropharynx is presented during a period separate from swallowing, it enhances cortical activity in the swallowing regions (Fraser et al., 2003; Hamdy et al., 2003; M. Power et al., 2004; Lowell et al., 2008), but does not benefit subsequent swallowing in dysphagic patients (M. L. Power et al., 2006). These approaches to stimulation, however, generally involve the placement of a device or probe into the oral cavity which interferes with eating food and liquids and can alter oral sensory function in patients already having oral sensory deficits.

Accordingly, there is a need for therapeutic methods and a device for enabling those who are afflicted with dysphagia or other conditions or disorders that affect the ability to properly swallow without interfering with oral function or altering oral sensory function.

SUMMARY

A device and methods for treating a subject with dysphagia or other neurological disease, neurological disorder, neurological injury, neurological impairment or neurodegenerative disease that affects voluntary motor control of the hyoid, pharynx, larynx, oropharyngeal area, is disclosed. The device and methods of the invention can also be used to treat a subject with a speech disorder.

A device of the invention generally comprises a vibrotactile stimulator for applying at least one stimulus to the outside surface of a subject's neck. The at least one stimulus comprises a vibrational stimulus, an auditory stimulus, a temperature stimulus, a visual stimulus, an olfactory stimulus, a gustatory stimulus, or a combination thereof. The vibrotactile stimulator comprises at least a vibrational transducer; a manual stimulation module to manually engage the vibrational transducer; an automatic stimulation module to automatically engage the vibrational transducer; and a manual counter and/or an automatic counter for determining the number of times the manual stimulation module and/or the automatic stimulation module is engaged.

In an embodiment, the vibrational transducer produces a wave having a frequency of about 50 Hz to about 70 Hz. In certain embodiments, the vibrational transducer produces a wave having a frequency of 59 Hz. In an embodiment, the automatic stimulation module comprises an automatic timer. The automatic timer can include an automatic clock to initiate the onset of the automatic stimulation module; an adjustable clock to initiate the automatic stimulation module at an adjustable interval of about 0.5 s to about 30 minutes; and an adjustable timer that allows for setting the duration of stimulation of about 100 ms to about 10 s.

A device of the invention also generally comprises a connector for attaching the vibrotactile stimulator to an outside surface of the subject's neck. The connector can be adjusted by an adjustment mechanism for positioning a contact section of the vibrotactile stimulator substantially over the subject's larynx. A device of the invention also generally comprises a switch control communicatively connected to the vibrotactile stimulator to selectively engage the manual stimulation module and the automatic stimulation module.

A device of the invention can also include one or more physiological sensors electrically coupled to the vibrotactile stimulator; a swallowing receptor comprising a piezoelectric stretch receptor; a battery, contained within the vibrotactile stimulator, acting as a power supply for the device; and a control box for selecting one or more of the stimulus mode, stimulus type, stimulus rate, and stimulus amplitude. The physiological sensors can include movement sensors, temperature sensors, skin color sensors, hematocrit sensors, oxygenation sensors, and blood pressure sensors. In one example embodiment, a swallowing receptor comprises a piezoelectric accelerometric movement sensor.

A device of the invention can also include a digital clock generator for producing an initial clock signal having a first frequency range; a digital decade counter for receiving the initial clock signal and producing sequential pulses having a second frequency range; and a motor responsive to the sequential pulses for producing vibrations on the subject's larynx, having a third frequency range. In an embodiment, the initial clock signal is adjustable and comprises a frequency. In an embodiment, the frequency of the clock signal comprises about one signal every 3 minutes to about one signal every 30 minutes. In an embodiment, the second frequency range is about 1 Hz to about 10 Hz, or about 20 Hz to about 75 Hz, or about 30 Hz to about 60 Hz with durations of about 10 ms to 500 ms. In an embodiment, the third frequency range is about 15 to about 200 Hz or between about 20 and about 100 Hz. The motor can include a planetary gearbox. In an embodiment, the motor produces a vibrational frequency of about 50 Hz to about 70 Hz.

Methods for treating a subject with dysphagia or other neurological disease, neurological disorder, neurological injury, neurological impairment or neurodegenerative disease that affects voluntary motor control of the hyoid, pharynx, larynx, oropharyngeal area, or hyolaryngeal complex disorder with a device of the invention is also disclosed. The methods of the invention can also be used to treat a subject with a speech disorder.

In one aspect, methods for inducing a swallowing reflex in a subject to prevent drooling and/or aspiration of the subject's own secretions are disclosed. The secretions can be saliva and/or mucus. The methods generally comprise applying a device of the invention to an outside surface of the subject's neck substantially over the subject's larynx and configuring an automatic timer to activate the vibrotactile stimulator to induce the swallowing reflex. In an embodiment, activation of the vibrotactile stimulator produces vibrations at a frequency of about 40 Hz to about 70 Hz and applies pressure of about 1 psi to about 14 psi to the subject's neck during an onset period. In an embodiment, the onset period comprises about 10 ms to about 1.5 s, about 50 ms to about 750 ms, or about 100 ms to about 500 ms. In an embodiment, an automatic timer of the device of the invention is configured to activate the vibrotactile stimulator at an interval of about once every 3 minutes to about once every 30 minutes.

In another aspect, methods for identifying a subject at risk of aspiration from their own secretions are disclosed. The methods generally comprise applying a device of the invention to an outside surface of the subject's neck substantially over the subject's larynx; downloading data from the vibrotactile stimulator after a period of use of the device by the subject; and analyzing to data to determine if the subject is at risk of aspiration from their own secretions. The subject activates the device to induce volitional swallowing and the device records the data to allow a health professional to determine if the subject is at risk.

In yet another aspect, methods for monitoring patient compliance with a training or therapy regime are disclosed. The methods generally comprise applying a device of claim 1 to an outside surface of the patient's neck substantially over the patient's larynx, wherein the patient activates the device to induce volitional swallowing; downloading data from the vibrotactile stimulator after a period of use of the device by the patient; and analyzing to data to determine the patient's compliance with the training or therapy regime.

BRIEF DESCRIPTION OF THE DRAWINGS

FIG. 15 shows that button press training alone can improve swallowing safety as the Total Score reduced significantly.

FIG. 19 is on a larger scale than FIG. 20. FIG. 19 shows that high motor levels of electrical stimulation (>8 mA) do not benefit swallowing in some patients with swallowing disorders.

FIG. 20 is auto scaled to the range of the data in the condition. Therefore the FIG. 16 is on a larger scale than FIG. 20. FIG. 20 shows that high motor levels (>8 mA) of stimulation do not benefit swallowing.

DETAILED DESCRIPTION

Figure 1:
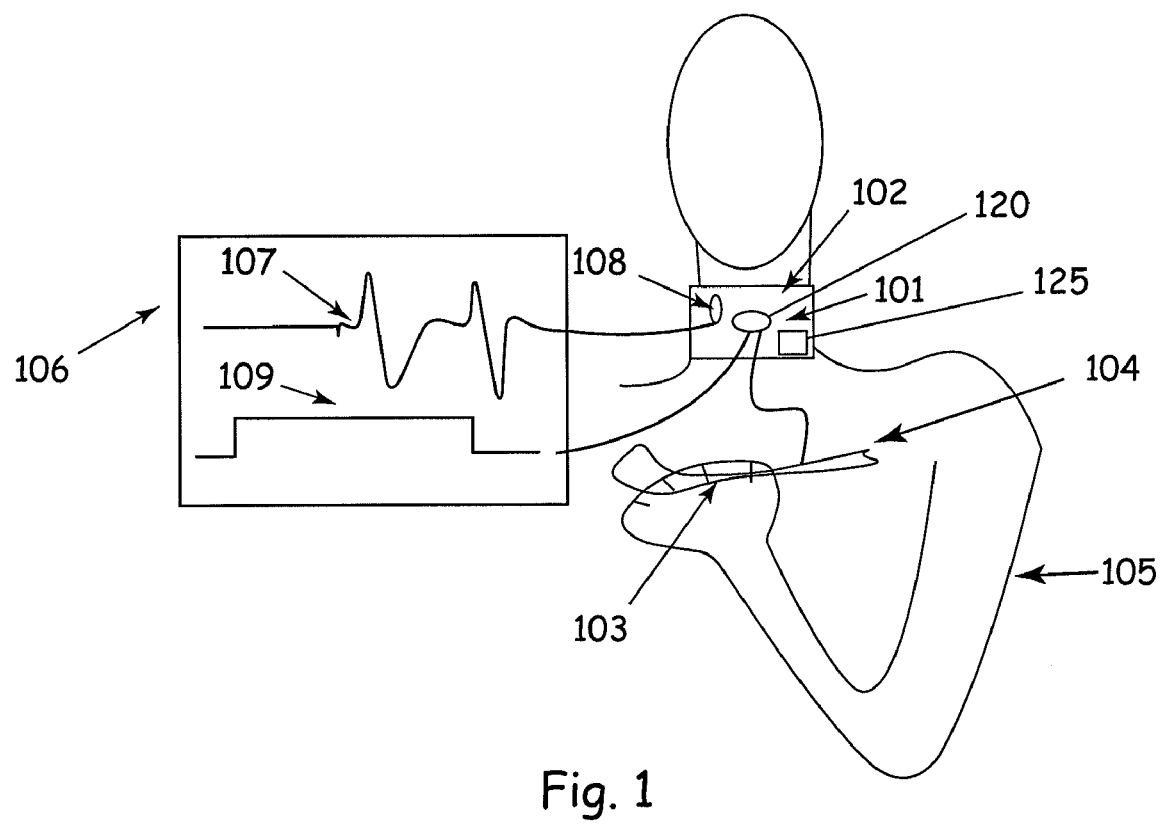
FIG. 1 is an example system incorporating a device for use in volitional swallowing retraining.

The present disclosure relates generally to systems and methods for treating and managing neurological disease co-morbidities and disorders affecting the volitional control of muscles that are involved in raising and lowering the hyoid/larynx and/or pharynx in the neck. Systems and methods that produce deglutition stimulation and vocalization stimulation and/or combinations of these are disclosed. In general, these types of stimulation may be volitionally coordinated and controlled electrically, mechanically, chemically or biologically. For example, in accordance with principles of the present disclosure, the combined use of button press training with simultaneous vibratory pressure stimulation on the neck region of the larynx is employed to facilitate voluntary control of swallowing. This method and systems of the disclosure are particularly useful for treating and managing subjects having dysphagia.

Others have attempted providing stimulation to areas that are reduced in sensory function to enhance swallowing in patients with dysphagia (Park, O'Neill, & Martin, 1997), and in normal volunteers (Theurer, Bihari, Barr, & Martin, 2005). For example, the device disclosed by Theurer et al. requires that a dental plate be constructed and placed over the lower teeth. This device interferes with mouth closing and therefore makes it difficult for patients to control liquid in their mouth. Electrical stimulation of the faucial pillars in the mouth requires a probe to be placed in the mouth, making it impossible for patients to swallow such that this method can only be used at a time separate from asking the patient to swallow (Fraser et al., 2003; Hamdy et al., 2003; M. Power et al., 2004). Therefore, placement of devices into the oral cavity is not optimal as such devices will interfere with eating food and liquids and alter the oral sensory function in patients (Theurer, Bihari, Barr, & Martin, 2005) who already have oropharyngeal sensory deficits (Hagg & Larsson, 2004; Aviv, Sacco, Mohr et al., 1997; Setzen et al., 2003).

One important aspect of the present disclosure is that the device of the invention is applied to an exterior surface of the throat area and not inside the mouth or the pharynx. A device placed inside the mouth or the oropharynx will interfere with eating. For example, the device disclosed by Park et al., (Park, O'Neill, & Martin, 1997) covers the mucosa in part of the mouth or the roof of the mouth thereby interfering with normal sensation for controlling the movement of the food or liquid in the mouth using sensory feedback between the tongue and the roof of the mouth.

Many patients with dysphagia already have oral sensory deficits (Logemann, 1993; Logemann et al., 1995). Providing stimulation to regions that are already impaired in sensation can be expected to provide less sensory facilitation of volitional and reflexive swallowing than sensory stimulation to unaffected areas. Therefore, the present disclosure is aimed at providing simultaneous sensory facilitation to areas unaffected by sensory deficits such as the skin overlying the throat area and the vibratory sensors in the musculature and cartilages in the throat area and the thyroid cartilage in particular. Vibratory stimulation of the thyroid cartilage and the sternothyroid muscle has already been shown to have powerful effects on voice (Loucks, Poletto, Saxon, & Ludlow, 2005). The methods and systems of the present disclosure differ from other previous approaches in that the patient initiates the stimulation themselves immediately prior to swallowing and such stimulation is to an area that will not interfere with oral and pharyngeal movement and sensation during swallowing.

A. Stimulator Systems and Devices

Referring now to FIG. 1, an example system 100 incorporating a device in accordance with the principles of the present disclosure is shown. More specifically, FIG. 1 depicts a device for treating dysphagia or a speech disorder. For example, in general, a band 101 may be wrapped around the neck for dysphagia treatment. The band 101 may include a vibrator 102 such that the vibrator 102 may be positioned over the larynx to provide sensory stimulation. In certain embodiments, a designated contact section 120 of the vibrator 102 is positioned to be in contact with the outside of a subject's throat over the larynx. Additionally, the band 101 can include an adjustment mechanism 125 for tailorable positioning of the contact section 120 over the subject's larynx. Upon activation of an actuator 103, such as a button, switch or other equivalent actuator communicatively connected to vibrator 102, on a utensil 104, such as a spoon, fork, or knife, held by the subject 105, the vibrator 102 is engaged and transmits vibrational energy to the throat and the larynx. Actuator 103 can be covered when not in use. In an embodiment, actuator 103 may be a button in a small cover that is reversibly slid over the top of a spoon handle or spoon handle shaped mount. Alternatively, the actuator 103 can be independent of the utensil. Thus, in one embodiment, actuator 103 is a remote switch that may or may not be physically connected to the stimulating device.

In certain embodiments, a device to control one or more vibrator operating can be provided. For example, a control box (not shown) having appropriate switches, knobs, or dials can be provided to set a stimulus type, a stimulus rate (set or increasing) and/or a stimulus amplitude (set or increasing). Additionally, the control box can include features to determine stimulus duration. For example, the control box can be configured to allow for stimulation for a specific duration of time upon activation of actuator 103 or as long as actuator 103 is depressed. In one example embodiment the duration of stimulation is about 6 seconds to about 25 seconds.

Referring still to FIG. 1, instructions can be provided to the subject 105 for practice of initiating the sensory stimulation immediately prior to the subject's 105 own initiation of a motor act such as swallowing. The initiation may be coordinated by viewing on a display screen 106 a movement feedback signal 107. The movement feedback signal 107 can be provided, for example, by a piezoelectric or pressure sensor 108 also contained in the neck wrap 101, which can be displayed on a display screen 106 when the motor movement begins. In one example embodiment, a piezoelectric accelerometric movement sensor is contained in the neck wrap 101. The signal 109 from the button 103, initiating sensory stimulation, can be presented on the same display screen 106 for the subject 105 and a trainer to observe when the actuator 103 was activated for sensory stimulation in relation to the onset of the motor act or swallow. In this manner, the subject can learn to optimize the timing of the sensory switch to occur about 600 ms to about 200 ms prior to the onset of their motor act of swallowing. It will be appreciated that actuation of the vibrator 102 via the actuator 103 may be accomplished via a hardwired connection or wireless telemetry. Similarly, communication between the movement sensor and the (display may be hardwired or by wireless telemetry to relieve the subject 105 from the hardwired devices.

Without wishing to be bound by any one theory for this embodiment, it is believed that such motor training produces concurrent brain activation due to sensory input that induces a central pattern generator in the patient's brain stem that produces the related effect of swallowing. It will be appreciated to those skilled in the art that this principle is applicable to many other neurological impairments, their associated motor act habituations and related sensory stimulations. Accordingly, the scope of the methods and systems of the present disclosure will be applicable to that a large variety of patients having various diseases and disorders.

Figure 2:
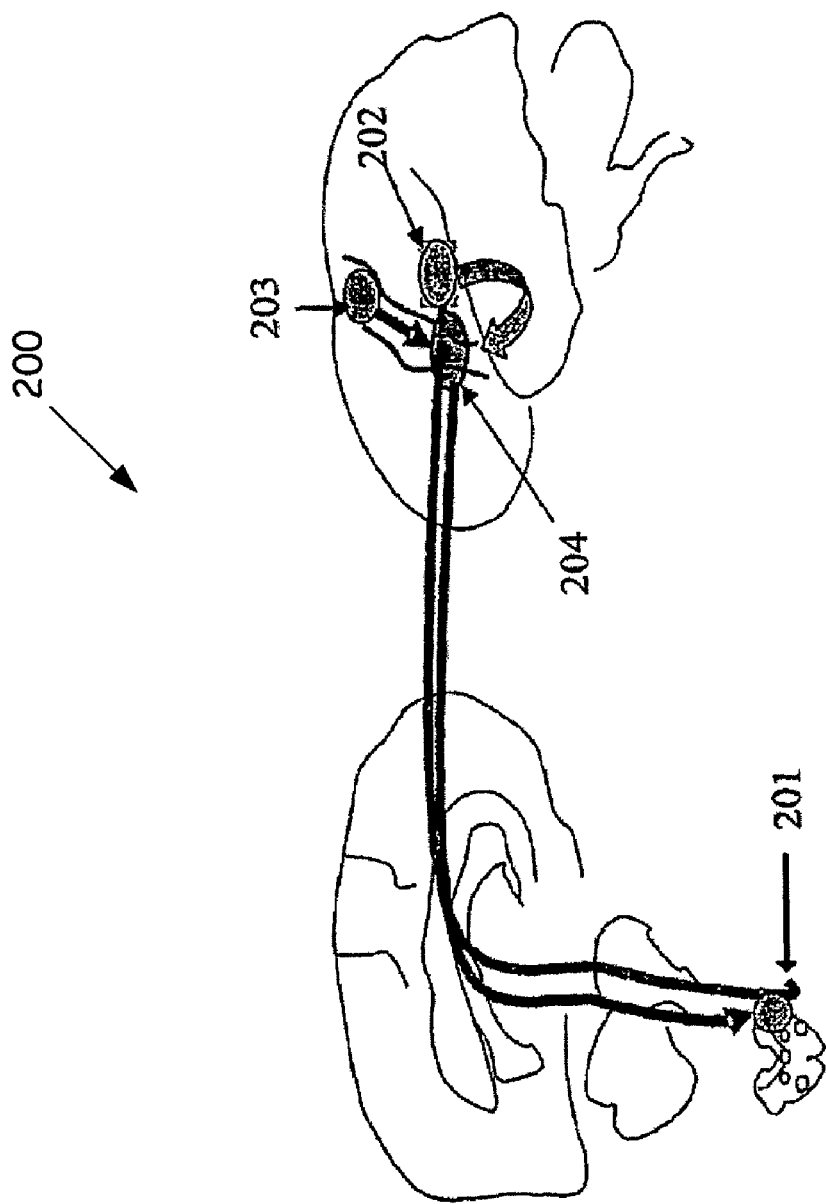
FIG. 2 is an example diagram illustrating the neural circuitry involved in the concurrent use of hand control and substitute sensory stimulation to enhance volitional swallowing.

Referring now to FIG. 2, an illustration 200 of the neural circuitry involved in the concurrent use of hand control and substitute sensory stimulation to enhance volitional swallowing is shown. More specifically, FIG. 2 illustrates the neural circuitry in using hand control 203 to trigger volitional swallowing 204 along with simultaneous sensory stimulation 201 which goes to the cortex 202. This is implemented after button press training described above with respect to FIG. 1. Elicitation of the swallowing reflex and safety in swallowing is dependent upon sensory feedback 201 to the brain from sensory mechanoreceptors in the upper airway. If sensory input is withdrawn, persons feel that they can no longer swallow and are at significant increase of aspiration during swallowing (Jafari et al., 2003). The neural circuitry enhances cortical motor control 202 of swallowing coincident with substitution of sensory input 203 from stimulation of the throat area to trigger brain stem circuitry to trigger reflexive swallowing 204 simultaneous with volitional swallowing.

Figure 4:
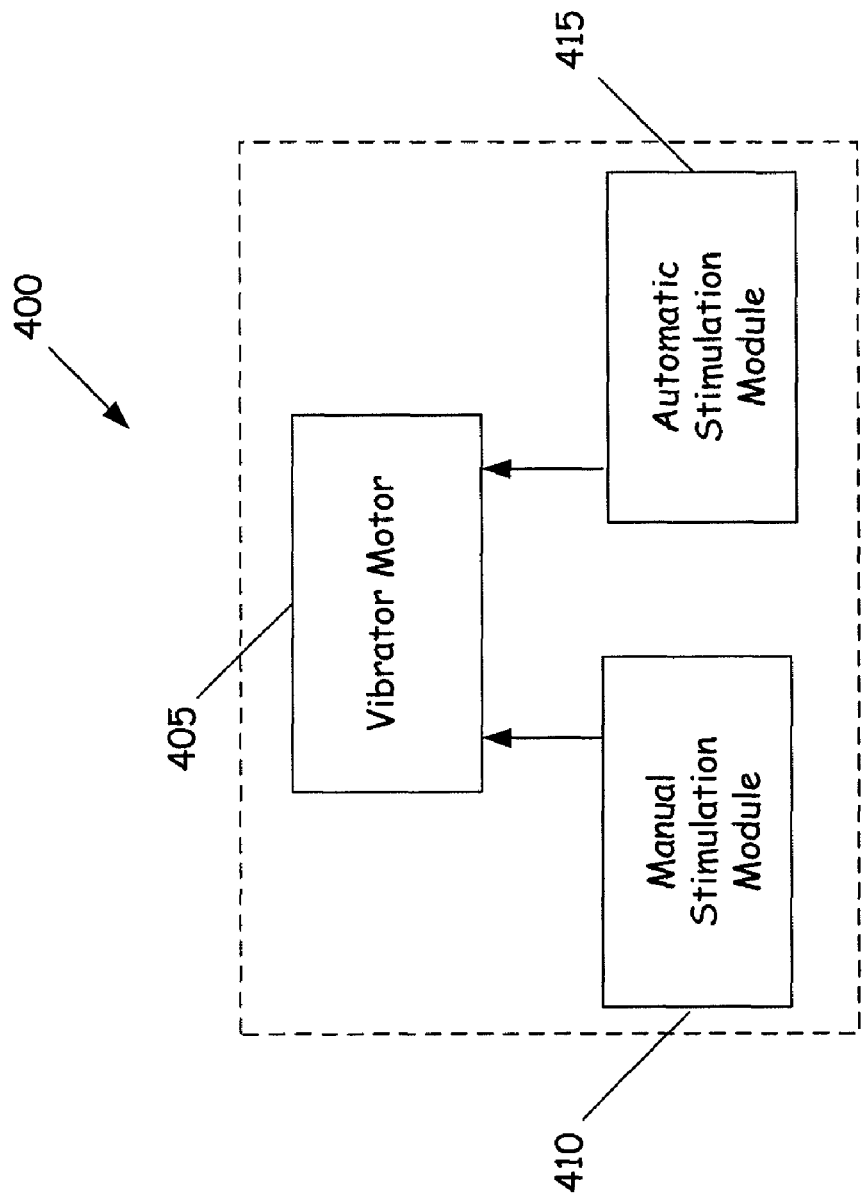
FIG. 4 is a general block diagram of a vibrotactile stimulator according to principles of the present disclosure.

Referring now to FIG. 4, a general block diagram of a vibrotactile stimulator 400 is shown according to principles of the present disclosure. The vibrotactile stimulator 400 can be used in example system 100. In certain embodiments, the vibrotactile stimulator 400 is pressed against the outside surface of subject's throat to stimulate the larynx such that with coordination, the vibrotactile stimulator 400 can be used to enhance volitional control of swallowing.

As described previously with reference to FIG. 1, the vibrotactile stimulator 400 may be secured or connected to a connector or a band that can be subsequently wrapped around the subject's neck. In this manner, a designated contact section of the vibrotactile stimulator 400 can be positioned on the subject's neck to stimulate the throat and larynx. Additionally, the connector can include an adjustment mechanism for a fine adjustment of the contact section over the subject's larynx. In certain embodiment, the adjustment mechanism shifts the position of the vibrotactile stimulator 400 within a circle having an area of about 0.01 to about 10 $cm^2$; about 0.25 to about 5 $cm^2$, or about 0.5 to about 2.5 $cm^2$.

In general, the vibrotactile stimulator 400 includes a manual stimulation module 410 operatively configured to allow a user to manually operate the vibrotactile stimulator 400 by pressing, or otherwise activating, an external actuator that communicatively connected to the vibrotactile stimulator 400. In general, the actuator can engage a vibrational transducer to transmit energy to a subject's larynx. In one embodiment, the actuator is a pushbutton ON switch that when pressed, or activated, energizes a vibrator motor 405 that vibrates at a desired frequency a periodic pressure wave that can transmit vibrational energy to the subject's larynx. In one embodiment, when the ON switch is released the vibration produced by the vibrator motor 405 is terminated. There is no delay between pressing the ON switch and the vibration to the throat area. In use, the manual stimulation module 410 may be engaged during activities such as eating, drinking, and swallowing to prevent aspiration with patients having dysphagia.

Additionally, in the example embodiment, the vibrotactile stimulator 400 includes an automatic stimulation module 415 operatively configured to automatically energize the vibrator motor 405. In certain embodiments, the automatic stimulation module 415 enables the subject or caregiver to programmably define vibrator motor 405 operating parameters such as duration, vibrational frequency, and amplitude. For example, the automatic stimulation module 415 can function to periodically energize the vibrator motor 405 to induce swallowing throughout the course of a day, thereby reducing saliva aspiration (and in general for saliva control) for subjects afflicted with dysphagia, for subjects with neurological disorders who have uncontrolled drooling, and for subjects with cerebral palsy who have uncontrolled drooling. In a preferred embodiment, the automatic stimulation module 415 includes an automatic timer circuit to facilitate the periodical energizing of the vibrational motor 405, as described in further detail below. In one aspect, the automatic timer provides for continuous practice throughout the day, which is required for rehabilitation of speech and/or swallowing disorders (Ludlow et al., 2008; Robbins et al., 2008). Automatic stimulation occurring at regular intervals of one every 3 minutes to one every 30 minutes will induce regular swallowing to eliminate drooling.

It will be appreciated to those skilled in the art that components of the vibrotactile stimulator 400 as described in the present disclosure may be implemented via hardware and/or software techniques. For example, the vibrotactile stimulator 400 may include a printed circuit board (PCB). The PCB may comprise a plurality of discrete electrical components such as transistors, capacitors, inductors, resistors and functional integrated circuitry such as a processor, a memory element, such as read-only memory (ROM) and/or random access memory (RAM), a field programmable logic array (FPGA) 1320, and input/output circuitry.

Figure 5:
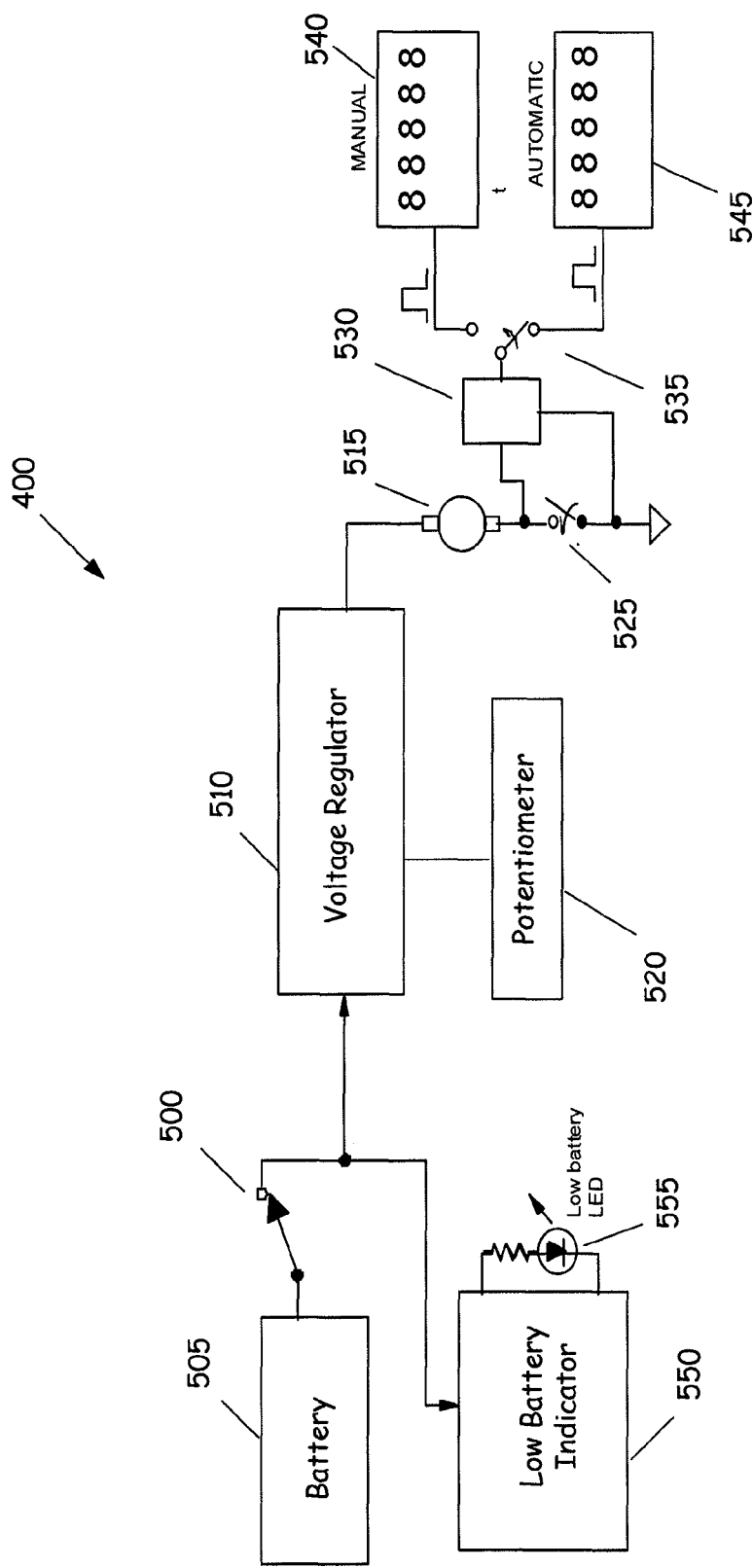
FIG. 5 is a more detailed block diagram of the vibrotactile stimulator of FIG. 4.

Referring now to FIG. 5, an example vibrotactile stimulator block diagram is shown as a possible implementation of the vibrotactile stimulator of FIG. 4. In general, upon engagement of a power switch 500, a battery 505 supplies power to a three terminal voltage regulator 510. In the embodiment as shown, the voltage regulator 510 is used as an adjustable current source to control vibrator motor 515 vibrational frequency. In practice, this may be accomplished by utilizing an external adjustable potentiometer 520.

Further, a switch control 525, such as a pushbutton, switch or other equivalent actuator is provided to enable the user to selectively engage the manual stimulation module 410 or automatic stimulation module 415. In certain embodiments the switch control 525 is communicatively connected to an external actuator such as a control box or a spoon. In the example embodiment, the switch control 525 is manipulated to electrically load a switch interface 530 such that a count select mechanism 535 is actuated. In this manner, a manual counter 540 is enabled when the user operates the vibrotactile stimulator 400 in the manual mode, and an automatic counter 545 is engaged when automatic stimulation is employed, as described further below. In a preferred embodiment, the automatic stimulation module 415 may be implemented with an automatic timer circuit such that the switch control 525 can be controlled by the automatic timer circuit to actuate the count select mechanism 535, thereby engaging the automatic counter 545 and energizing the vibrator motor 405.

In the example embodiment the counters 540, 545 are internally mounted to the vibrotactile stimulator 400. The manual counter 540 records the total number of times a subject engages the manual stimulation module 410. In a similar manner, the automatic counter records the number of times the automatic stimulation module 415 is engaged. Subsequently, the counters 540, 545 may be interrogated, or equivalently read, and reset manually after the total number of counts are recorded. In alternative embodiments, a wireless data interrogation using one of many technologies, such as Blue Tooth, may be performed to transfer the information to an external application. The quantitative information provided by the counters 540, 545 may provide, for example, an investigator or caregiver quantitative information regarding patient compliance and information regarding the effectiveness of the vibrotactile stimulator 400. As patient compliance is generally low, around 50% (Portone et al., 2008), it is important to the rehabilitation process to identify poor compliance particularly in the management of dysphagia, a life threatening disorder. Identification of poor compliance allows the therapist to intervene to assure proper use of the device by the patient and their caregivers.

In certain embodiments, the manual counter 540 and the automatic counter 545 can be provided with their own internal power supplies so that cumulative counts are not lost when the power switch 500 is disengaged. Additionally, the vibrotactile stimulator 400 may include a low battery indicator 550 such that if the battery 505 voltage drops below a specified voltage level an indicator specifying that event is generated. In the example embodiment an LED "Low Battery" indicator 555 comes on.

Figure 6A:
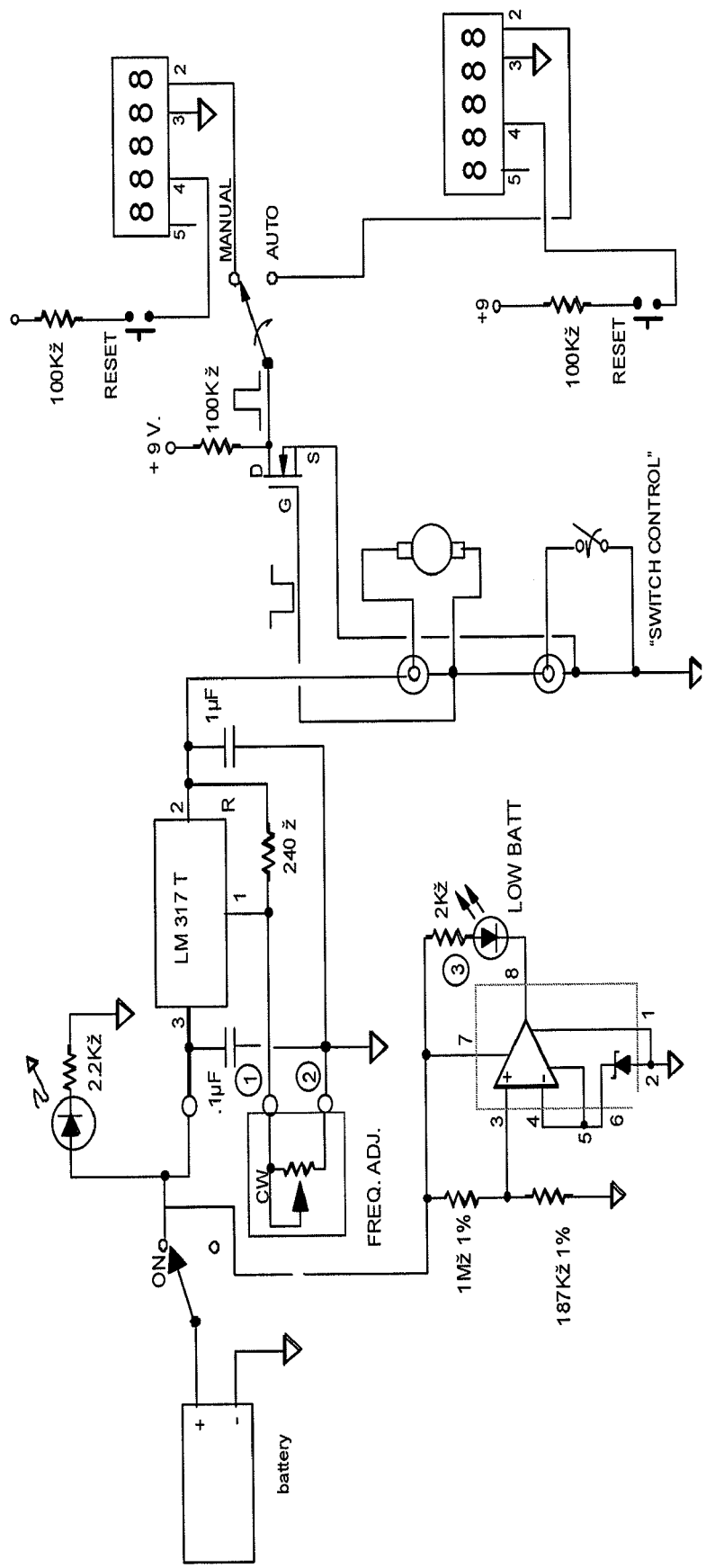
FIG. 6a is an example circuit diagram of the vibrotactile stimulator of FIG. 5 including a manual and an automatic counter.
Figure 6B:
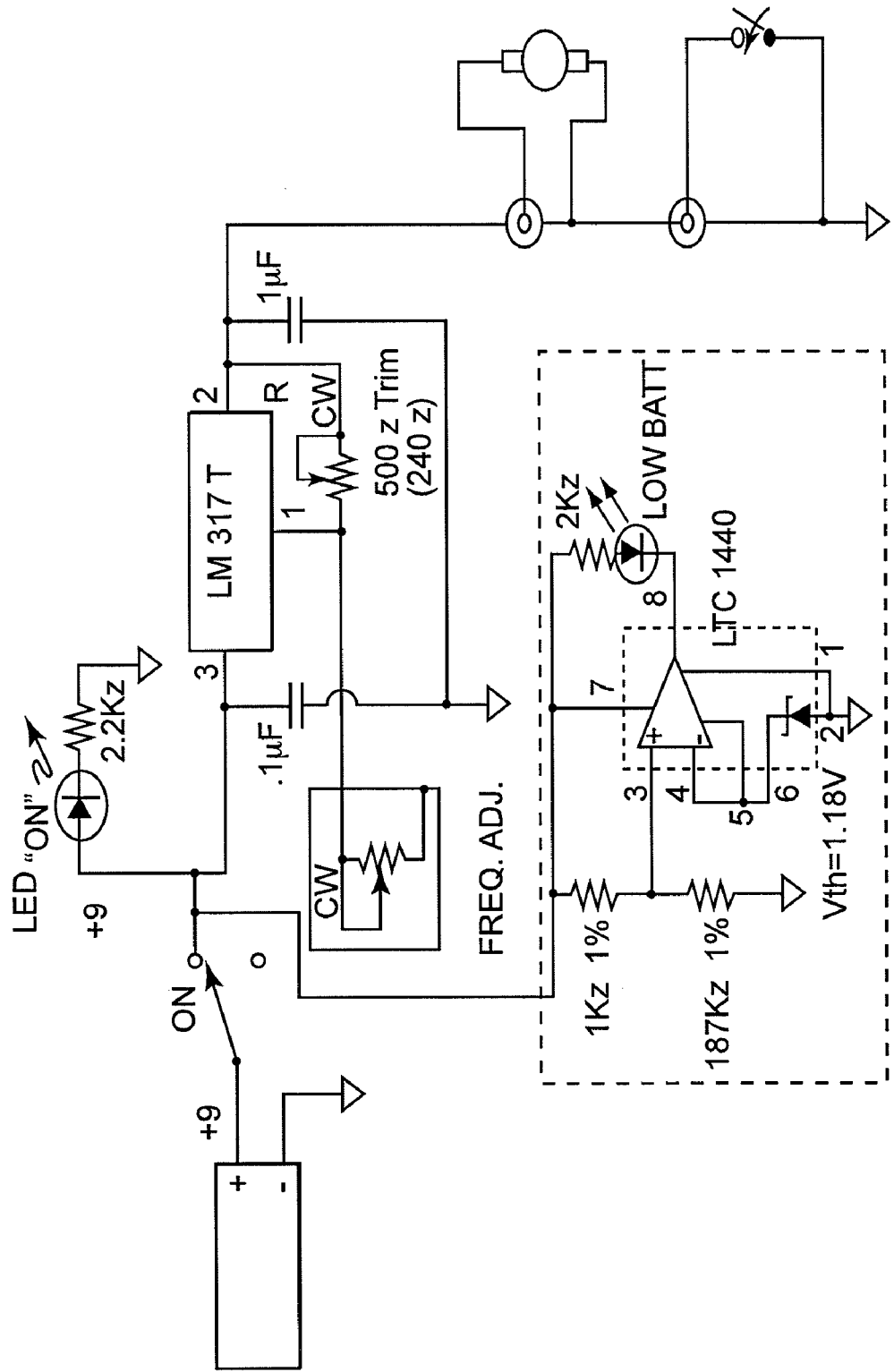
FIG. 6b is an example circuit diagram of the vibrotactile stimulator of FIG. 5 without a manual and an automatic counter.

Referring now to FIG. 6a, a circuit diagram 600 is shown illustrating one embodiment of a vibrotactile stimulator block diagram of FIG. 5. It will be appreciated to those skilled in the art that example circuit diagram 600 is only an example circuit architecture and that the vibrotactile stimulator 400 may be implemented via any suitable architecture. In the example embodiment both passive and discrete electrical components are chosen such that component attributes and tolerances fit a known specification. An alternative example circuit diagram 605 of the vibrotactile stimulator block diagram of FIG. 5 is shown in FIG. 6b.

Figure 7:
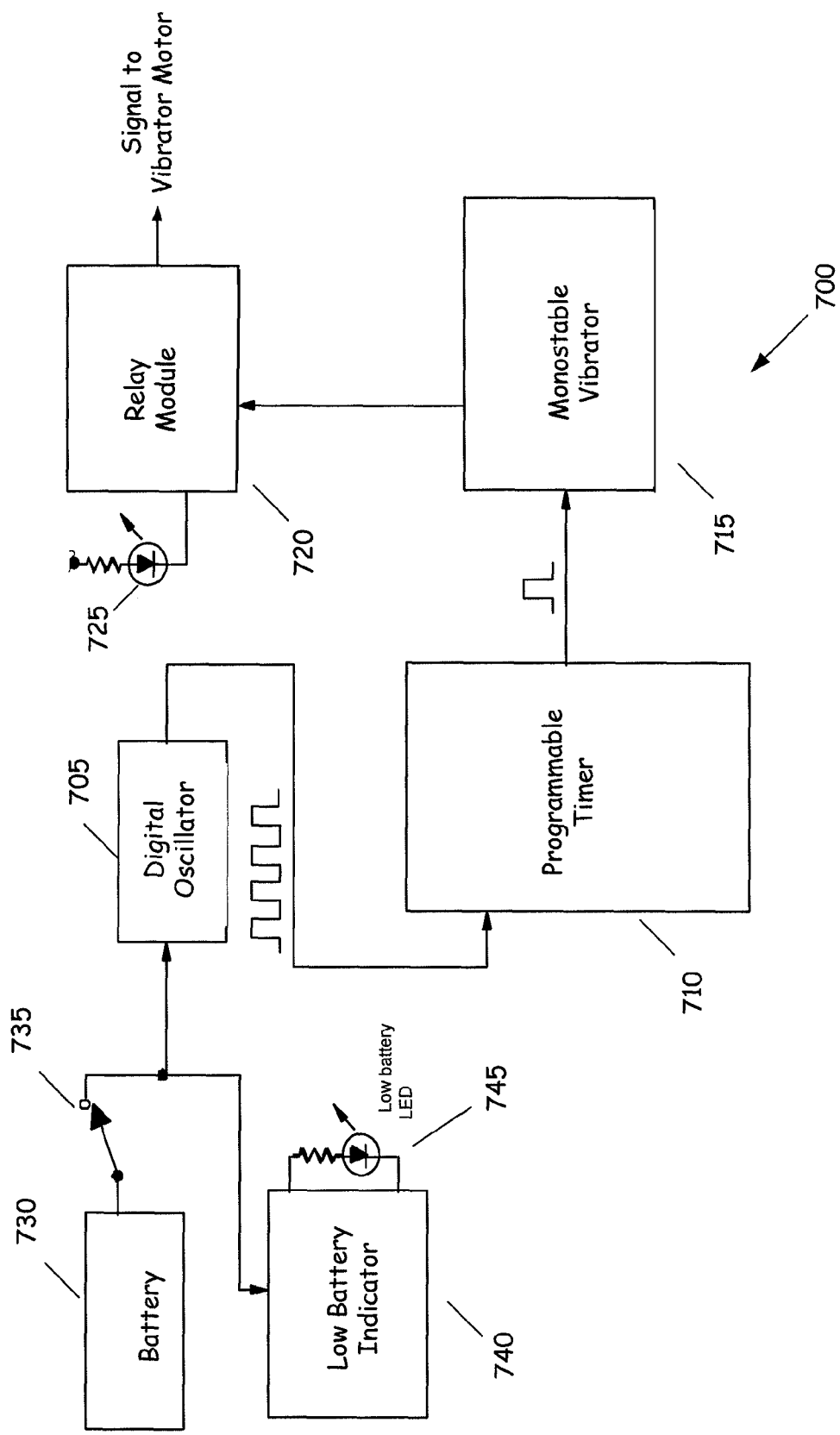
FIG. 7 is an example automatic timer circuit block diagram.

Referring now to FIG. 7, a block diagram of an automatic timer circuit 700 shown. In general, the automatic timer module is communicatively connected to the vibrotactile stimulator 400 as shown in FIG. 4. As previously mentioned, the automatic timer circuit 700 may actuate the count select mechanism 535, thereby engaging the automatic counter 545 and energizing the vibrator motor 405 for a predetermined period of time. In the example embodiment the automatic timer circuit 700 comprises of a digital oscillator 705 having an adjustable oscillating frequency of about 2.2 Hz to about 28 Hz. The output signal of the digital oscillator 705 is routed to a programmable timer 710 set to divide the periodic digital input signal by 4096. The input clock frequency from the digital oscillator 705 to the programmable timer 710 will determine when an output pulse is generated. In the example embodiment, the output pulse period may be generated in a range from about 3 to about 30 minutes. Subsequently, the programmable timer 710 output pulse triggers an adjustable monostable multivibrator 715. An output pulse width of the adjustable monostable multivibrator 715 sets the "On" time for the vibrator motor 515 (as shown in FIG. 5) by energizing a relay through a transistor switch. In the example embodiment, the transistor switch and relay control is integral to relay module 720. An LED 725 indicates that the relay has been activated, which is used to energize the vibrator motor 515 in the automatic mode. In an example embodiment, the selected time period may be about 5 to about 15 seconds.

In general, the automatic timer circuit 700 is powered by a battery 730 or other equivalent power source and a power switch 735. Additionally the automatic timer circuit 700 may also include a low battery indicator 740 such that if the battery 730 voltage drops below a specified voltage level an indicator specifying that event is generated. In the example embodiment an LED "Low Battery" indicator 745 comes on. It will be appreciated that the battery 730, the power switch 735, the low battery indicator 740 and the LED 745 may be used to power the vibrotactile stimulator 400 as shown in FIG. 5.

Figure 8A:
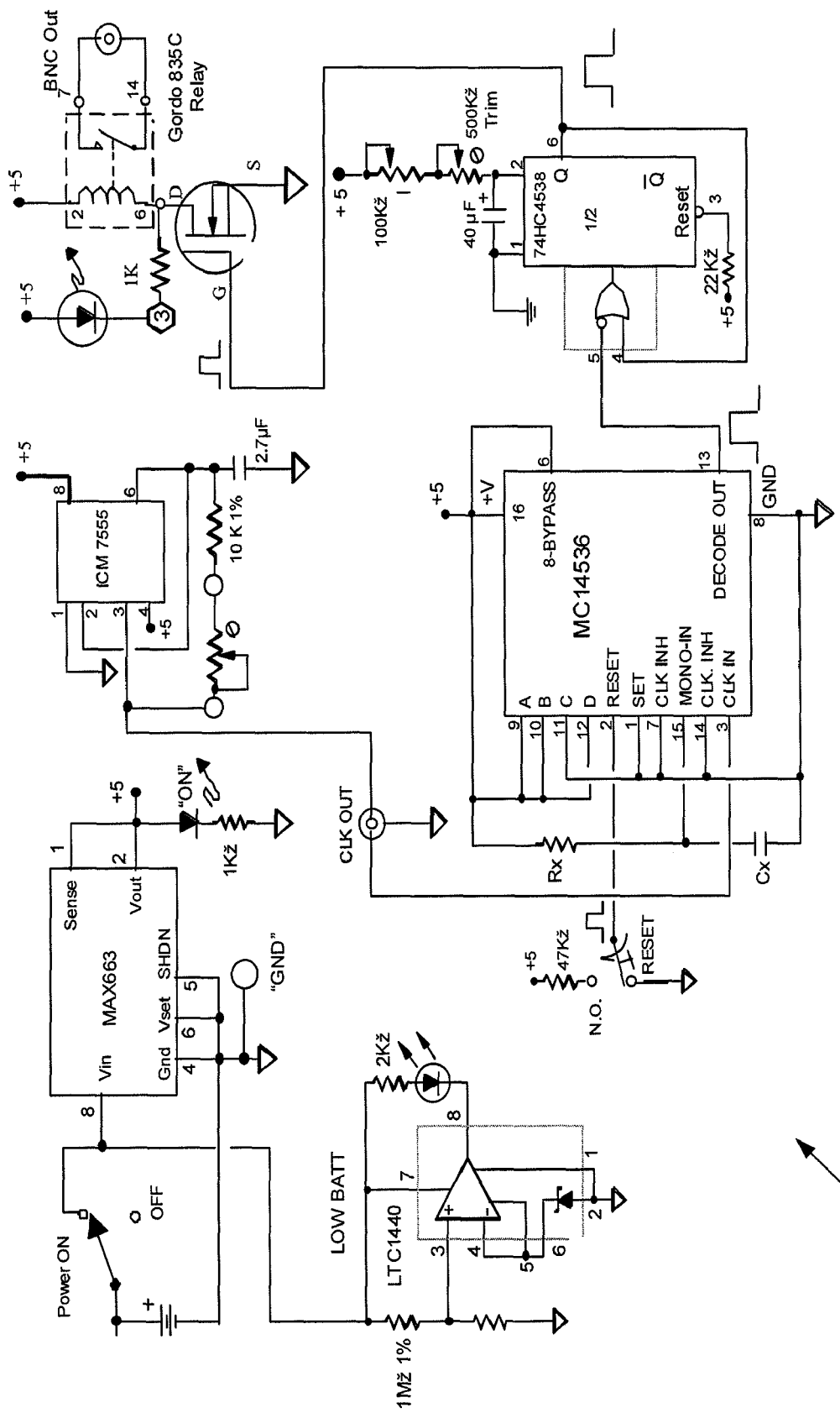
FIG. 8a is example circuit diagram of the automatic timer circuit as shown in FIG. 7.
Figure 8B:
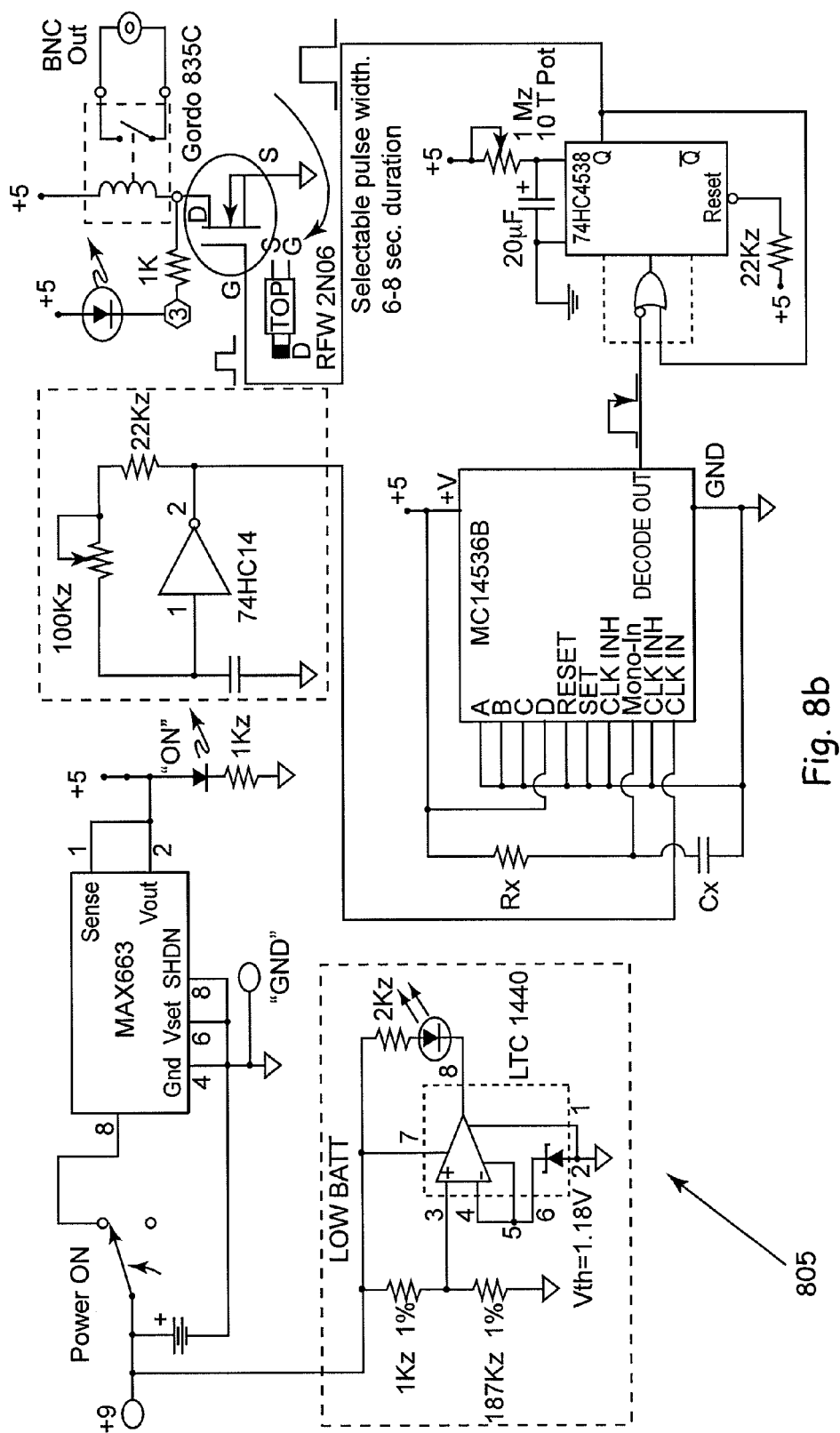
FIG. 8b is an alternative example circuit diagram of the automatic timer circuit as shown in FIG. 7.

Referring now to FIG. 8, a circuit diagram 800 is shown illustrating a one embodiment of the automatic timer circuit as shown in FIG. 7. It will be appreciated to those skilled in the art that example circuit diagram 800 is only an example circuit architecture and that the automatic timer circuit 700 may be implemented via any suitable electrical architecture. Additionally, in the example embodiment both passive and discrete electrical components are chosen such that component attributes and tolerances fit a known specification. An alternative example circuit diagram 805 of the automatic timer circuit as shown in FIG. 7 is shown in FIG. 8b. In certain embodiments, the manual counter 540, the automatic counter 545, and the automatic timer circuit 700 can be incorporated into a single functional counter and timer module that is mounted internally and communicatively connected to the vibrotactile stimulator 400.

Figure 9:
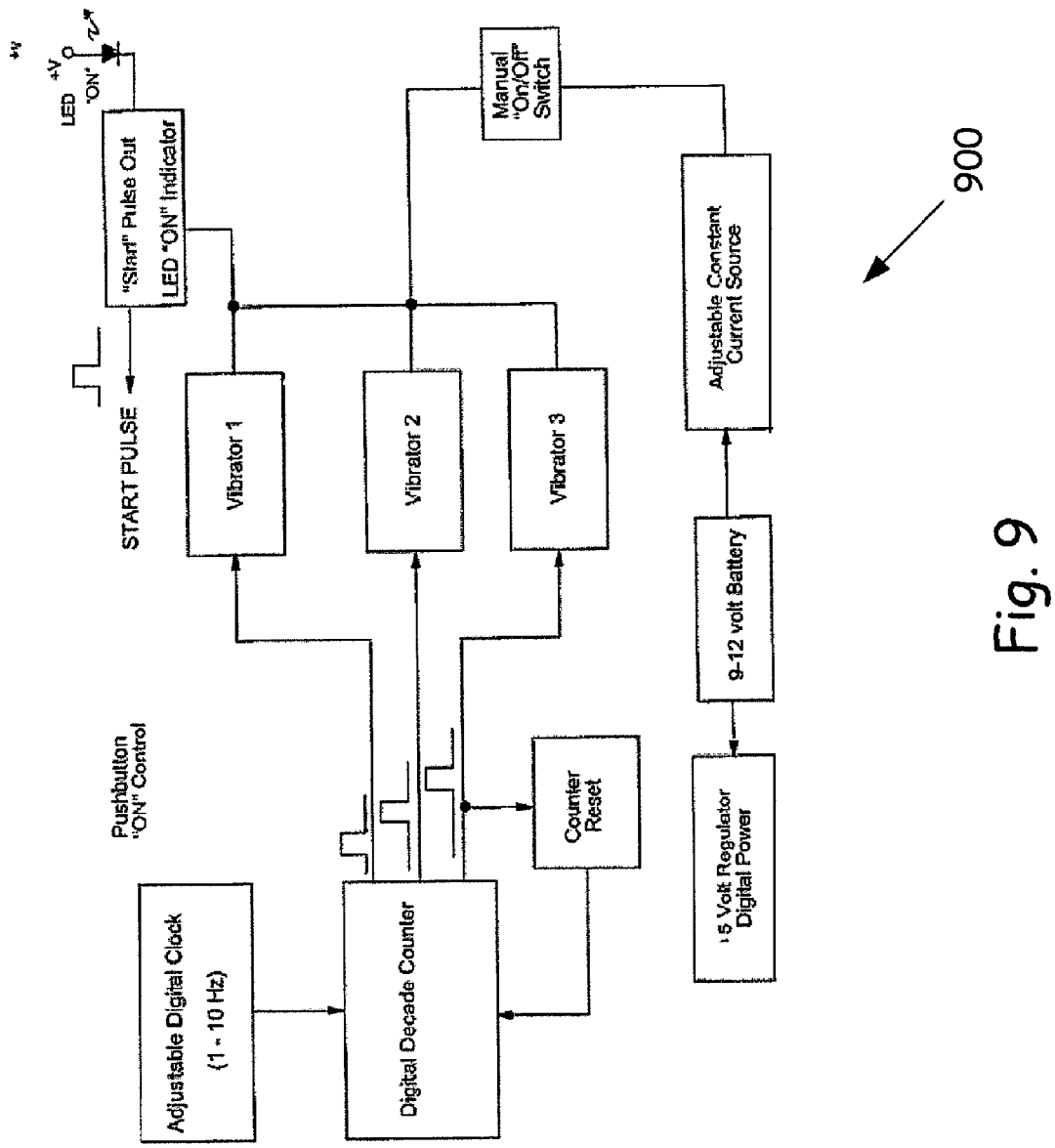
FIG. 9 an alternative embodiment of a vibrotactile stimulator of the present disclosure.

Referring now to FIG. 9, an alternative embodiment of a vibrotactile stimulator 900 is shown. In general, the vibrotactile stimulator 900 is a battery-powered device that sequentially activates one or more small DC vibrator motors as described herein. An adjustable digital clock can set the timing for separate events. The clock frequency can be adjusted between about 1 and about 10 Hz. This clock, in conjunction with a digital decade counter, generates sequential pulses that control the individual vibrators "On" and "Off" duration. At the end of the pulse cycle, a short reset pulse is generated to reset the decade counter and begin the next cycle of pulses.

A subject can control the vibrotactile stimulator 900 by pressing an external pushbutton "ON" switch. The switch will also activate an LED indicator light and will generate a digital pulse that can be used for coordinating various recording devices. When the button is released, the vibration pulses will stop. Preferably, there is no perceived delay between pressing the "On" switch and the first vibration to the throat.

Figure 10:
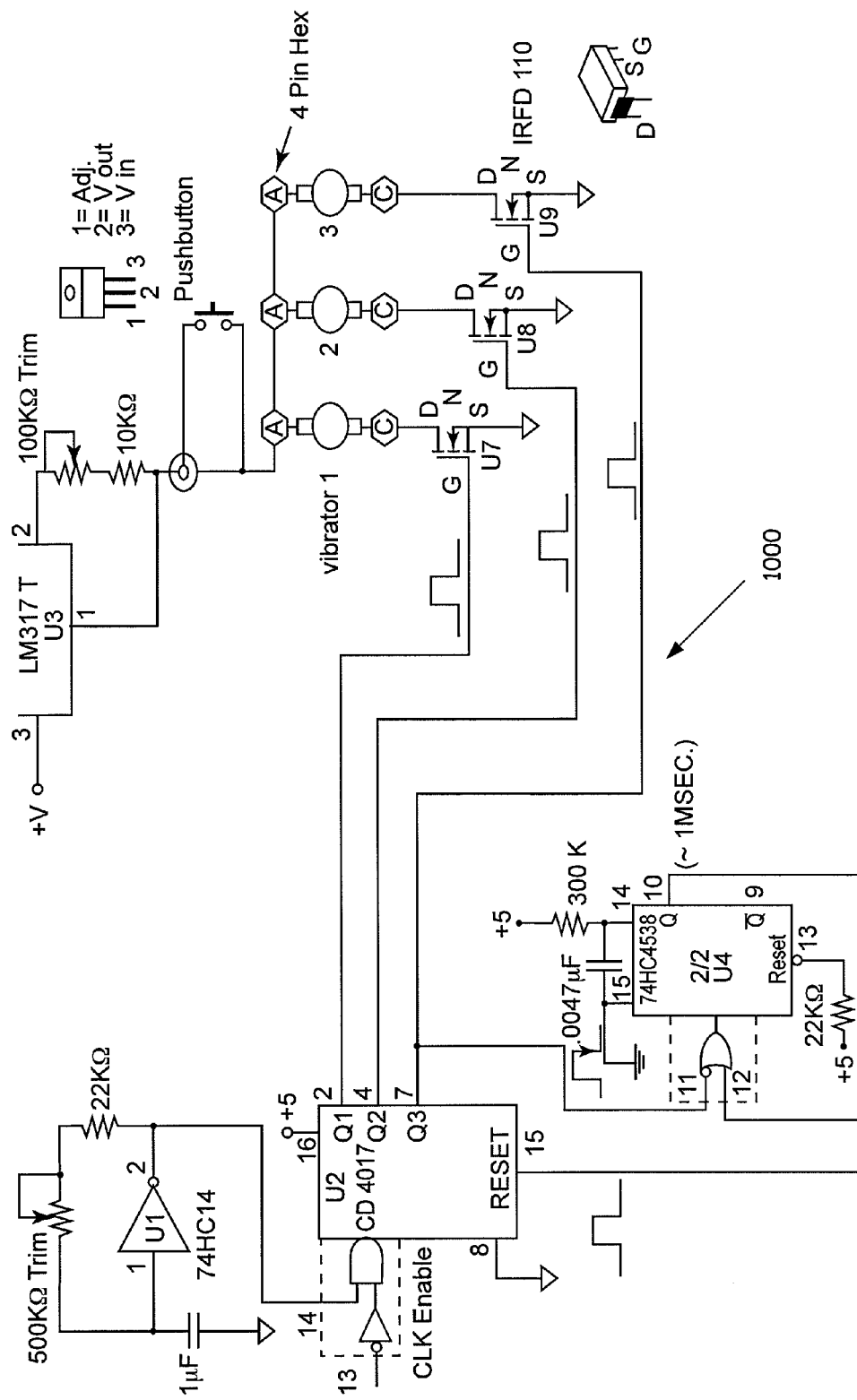
FIG. 10 is an example circuit diagram of the vibrotactile stimulator shown in FIG. 9.
Figure 11:
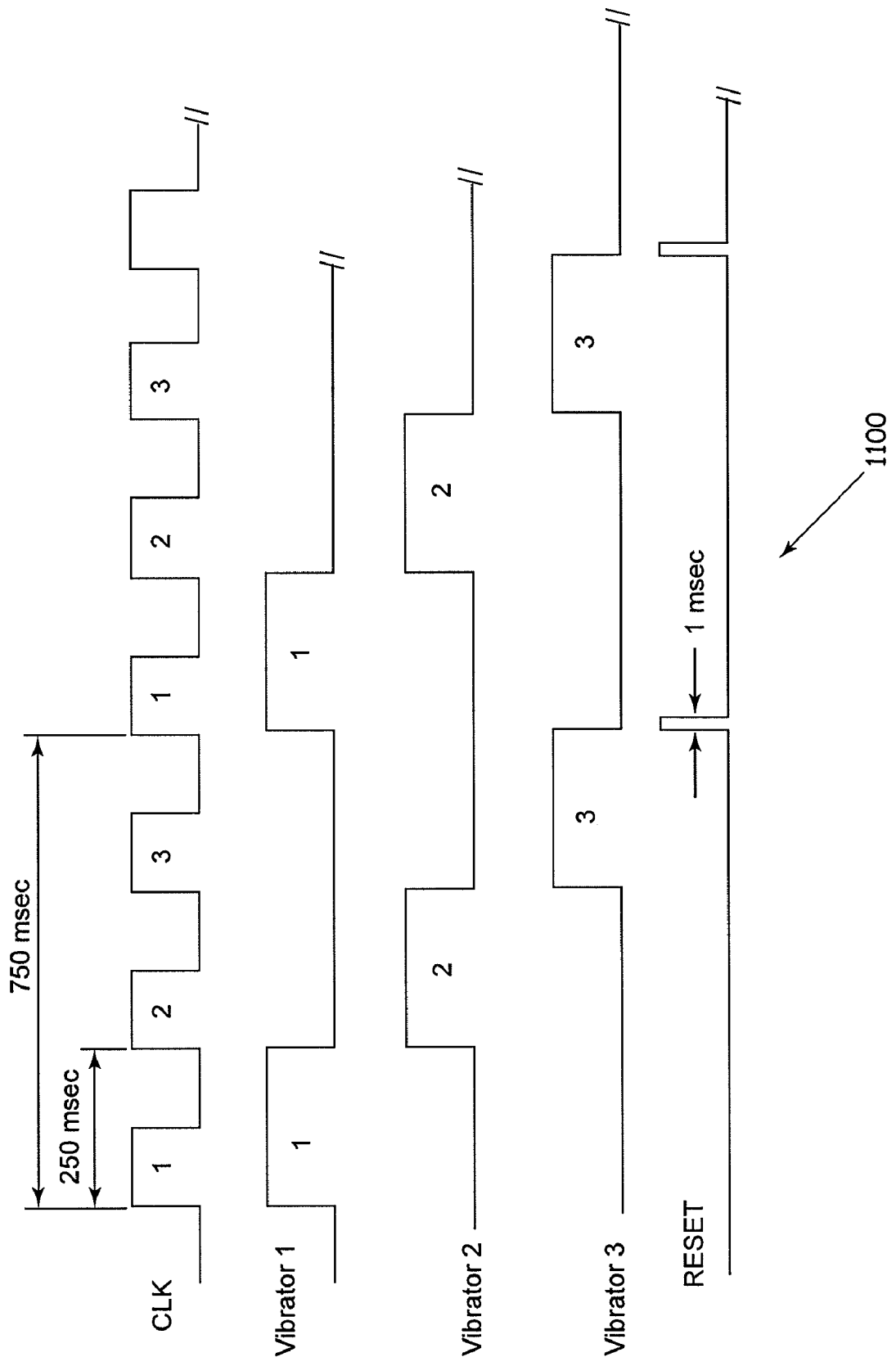
FIG. 11 is a diagram depicting a clock based sequential vibrator control as implemented with the vibrotactile stimulator of FIG. 9.
Figure 12:
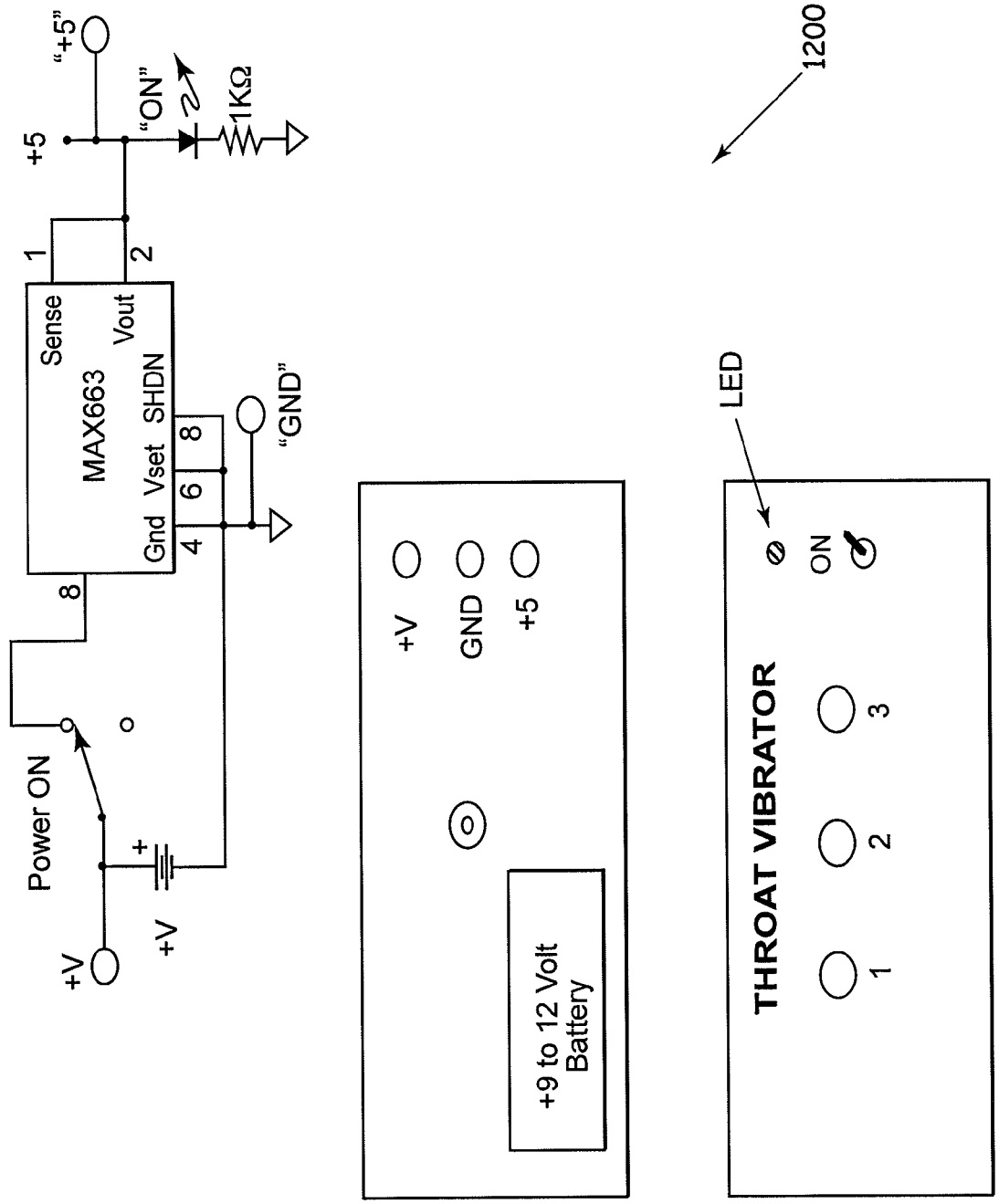
FIG. 12 is a diagram of the controller box for the vibrotactile stimulator as shown in FIG. 9.
Figure 13:
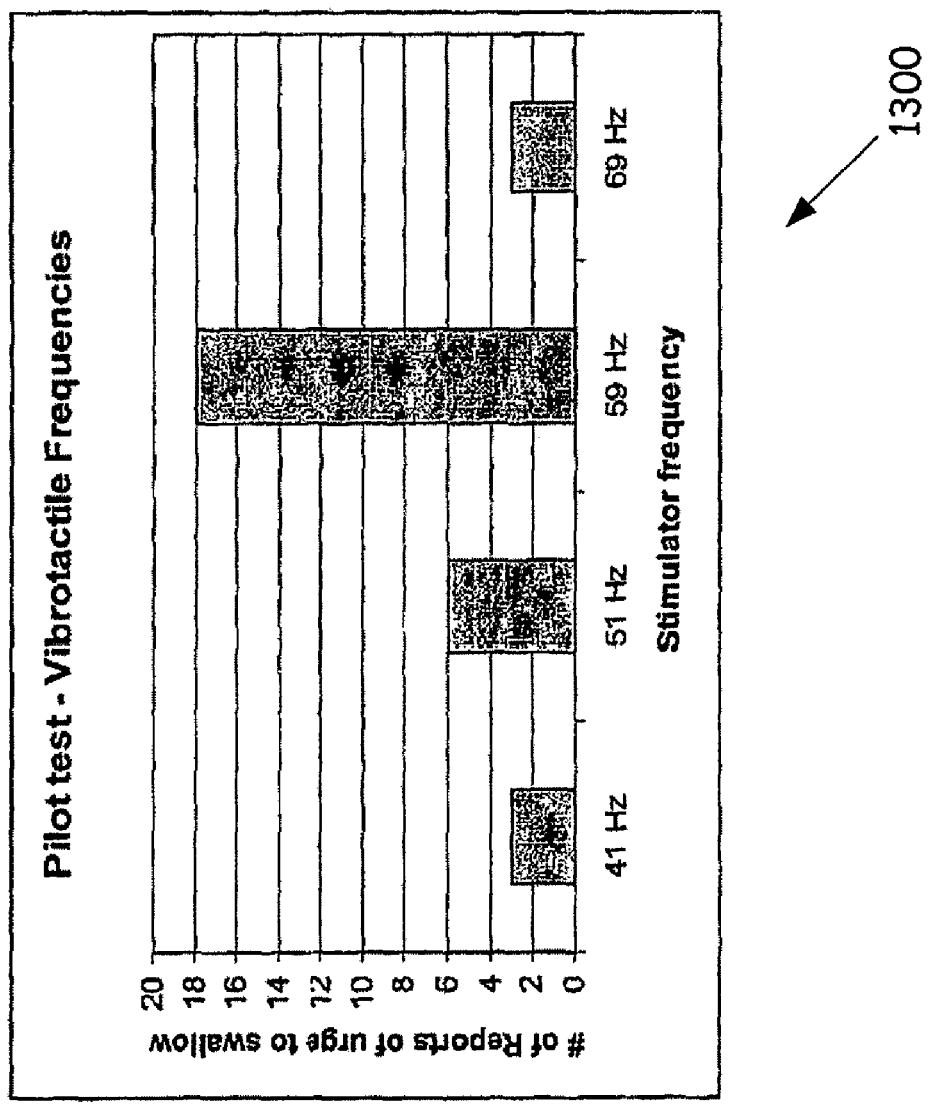
FIG. 13 is a plot illustrating that vibratory stimulation to the skin over the throat at about 59 Hz produces the most frequent reports of an urge to swallow.
Figure 14:
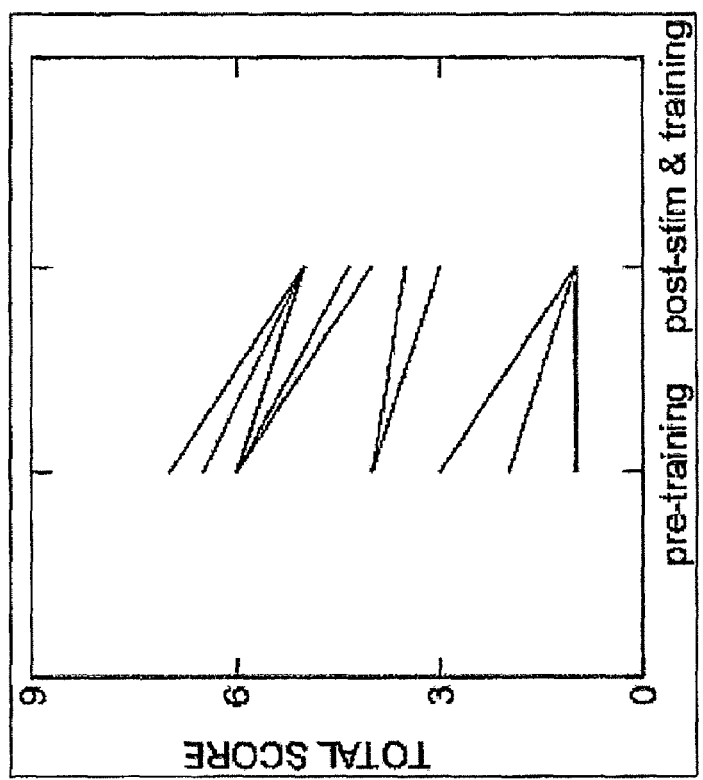
FIG. 14 is a graph showing individual patient pre-training baseline Total Score without stimulation or button press training representing the degree of risk of aspiration during swallowing and post-training Total Score following button press training for coordinating swallowing with intramuscular stimulation. An increased score represents a greater risk of aspiration during swallowing.
Figure 15:
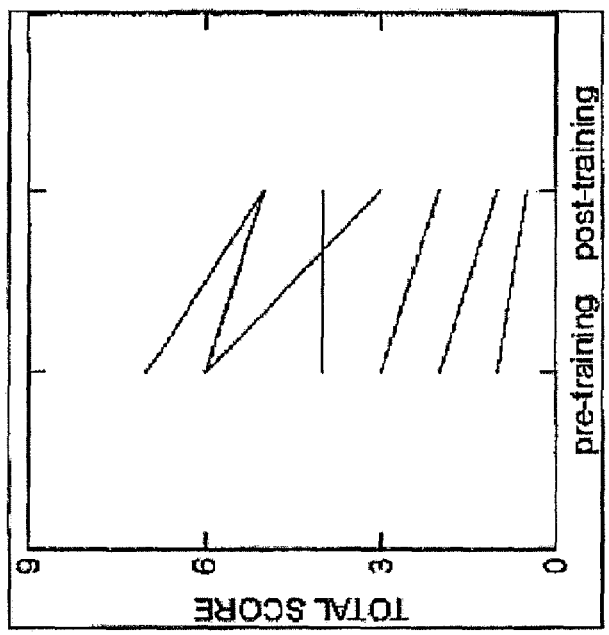
FIG. 15 is a graph showing individual patient pre-training baseline swallowing NIH safety score at baseline before button press training (an increased score represents a greater risk of aspiration during swallowing and post-training). Total Score following button press training for coordinating swallowing.

Referring now to FIG. 10, a diagram of an example circuit 1000 of the vibrotactile stimulator 900 as shown in FIG. 9 is depicted. Additionally, FIG. 11 is a diagram 1100 depicting a clock based sequential vibrator control as implemented with the vibrotactile stimulator 900 of FIG. 9. Further still, FIG. 12 depicts a diagram of the controller box 1200 for the vibrotactile stimulator 900 as shown in FIG. 9. The controller box 1200 may set one or more vibrotactile stimulator 900 operating parameters. For example, an operating parameter may include a stimulus type, a stimulus rate (set or increasing) an amplitude (set or increasing), or a combination thereof. Additionally, the control box may be configured to allow for stimulation for a specific duration upon activation of the button or as long as the button is depressed. In an embodiment, the duration of stimulation is about 2 seconds to about 6 seconds.

Referring now to the vibrator motor as utilized in the vibrotactile stimulator 900 as shown in FIG. 9 and in the vibrotactile stimulator 400 as shown in FIG. 4. In operation, a vibrator motor vibrating frequency of about 30 Hz to about 60 Hz is particularly effective in eliciting the swallowing reflex. The vibrator motor may be a low voltage DC motor with a planetary gearbox utilized to generate the effective frequency.

In operation the gearbox reduces the output rotation per minute (RPM) to the desired range and increase the available torque. An eccentrically loaded mass is attached to the output shaft to generate the vibration. The mass weight can be changed to increase or decrease the vibration amplitude. In an embodiment, a lightweight, sealed aluminum tube encapsulates the motor assembly. Further, in certain embodiments the vibrator motor may utilize a sleeve shaft for the output shaft. In alternative embodiments the vibrator motor may utilize a ball bearing shaft for the output shaft.

In use, one or more vibrator motors can be placed on the front of the neck over the region of the thyroid cartilage. The one or more vibrator motors may be held in place by a rigid/semi-rigid holder or one or more straps. The vibrators may be arranged on the inside of the holder to suit the neck dimensions of the individual patient/user. An elastic strap may be attached to the outside of the holder and is wrapped to attach in the back of the patient/user's neck to hold the holder in place. A small, battery powered portable box connects to the button that is pressed to drive the vibrators. In preferred embodiments, the device is supplied to the patient/user who is trained in its use by a speech-pathologist or other professional with knowledge of swallowing, speech or voice disorders.

The stimulation device of the invention can be covered by a disposable cover, such as a plastic or a cloth cover. Stimulators may be contained within a stretchable device such as a wrap with Velcro and is adjustable for individual patient bodies. Vibrator and electrical stimulators are preferably positioned close to the skin. In another embodiment, the stimulation device of the invention includes one or more sensors of physiology, such as temperature, skin color, hematocrit, oxygenation, blood pressure and the like. In an embodiment the device reports results by a display and or by electromagnetic transmission and monitors and/or records swallowing events. For example, a device of the present invention can monitor the presence (and optionally depth) of a swallowing event via a piezoelectric stretch receptor or other sensor on or in the band around the neck, and/or at the surface over the larynx. (See Holzer and Ludlow, 1996; Burnett et al, 2005).

B. Methods and Uses

The systems and devices of the invention can be used to treat a number of conditions and disorders including, but not limited to, stroke, cerebral hemorrhage, traumatic brain injury, dysphagia, post surgery to brain, Parkinson's disease, multiple sclerosis, birth defects, ALS, cerebral palsy, CNS injury, supranuclear palsy, and any other neurological disease, neurological disorder, neurological injury, neurological impairment or neurodegenerative disease that affects voluntary motor control of the hyoid, pharynx, larynx, oropharyngeal area, or hyolaryngeal complex. Neurological impairments that are contemplated include reflex actions that involve interactions between afferent and efferent paths, at the spinal cord or in the brain stem, as well as higher order interactions in the primary motor cortex of the hemispheres. The systems and methods of the present disclosure apply to patients who have lost or partially lost the ability to voluntarily control motor functions but also to patients who were born with birth defects that have prevented them from having voluntary motor control, such as cerebral palsy. The systems and methods of the present disclosure are also applicable to treating various speech motor control disorders such as stuttering and laryngeal dystonia.

The term "motor control" as used herein refers to the ability to control muscle activity at will. For instance, in one embodiment, the invention is applicable to the ability to swallow at will. Thus, patients with dysphagia, which is the complete or partial loss of the ability to swallow, can be treated with the methods of the present invention. In an embodiment, the disease or disorder reduces or delays motor control of swallowing and/or results in delayed or reduced elevation of the hyolaryngeal complex, which does not allow the patient to prevent food or liquid from entering the airway.

The methods of the invention generally comprise stimulating a substitute site for the area with a system or device according to the invention, thereby triggering the motor control of the affected area. The term "recovering" as used herein includes within its meaning obtaining the ability to volitionally control motor functions. "Volitionally" as used herein means at the will of the patient. A "substitute site" as used herein means an area of the body that is capable of eliciting a desired reflex but is not a sensory region that is able to elicit reflex in impaired patients.

Subjects are often not responsive to stimulation in the oral and pharyngeal cavities but remain sensate to vibratory stimulation to the areas of the human head which include anatomical structures (e.g., muscles, nerves or connective tissue) that work in concert to affect deglutition. By providing sensory stimulation to sensate areas on the throat, substitute stimulation can be used to enhance the volitional elicitation of swallowing. For example, patients with dysphagia following neurological disease usually have sensory loss in the oropharyngeal area (Aviv et al., 1996; Aviv, Sacco, Mohr et al., 1997; Aviv, Sacco, Thomson et al., 1997) which is normally required to be sensate in order to elicit safe swallowing without aspiration in normal volunteers (Jafari, Prince, Kim, & Paydarfar, 2003). The present invention uses sensory triggering in "substitute sites" to enhance the elicitation of reflex and volitional swallowing, such as stimulation of afferents from the laryngeal area contained in the superior laryngeal area (Jean, 1984), (Dubner, Sessle, & Storey, 1978), (Dick, Oku, Romaniuk, & Cherniack, 1993; Ootani, Umezaki, Shin, & Murata, 1995).

Basic studies suggest that the second order neurons excited by afferents in the superior laryngeal nerve are selectively excitable at particular frequencies (Mifflin, 1997) and that stimulation around 30 Hz may be preferred for exciting the swallowing system in the brainstem (Dubner, Sessle, & Storey, 1978). Patients are often not responsive to stimulation in the oral and pharyngeal cavities but remain sensate to vibratory stimulation to the throat area including the skin and laryngeal cartilages underlying the skin. Thus, the throat is a substitute site and by providing sensory stimulation to the throat, enabling swallowing "at will" or volitional swallowing may be elicited.

The site for stimulation can be adjusted depending upon the desired motor control. One of skill in the art, such as a treating physician or other allied health professional with experience with the disease causing the motor impairment will readily understand where to locate the stimulation. In an embodiment, the affected area is the area of the body responsible for swallowing, speech, or voice. In an embodiment, the affected area is the oropharyngeal area. In an embodiment, the substitute site is the area of the throat over the larynx. In an embodiment, the recovered motor control is volitional swallowing.

By providing a vibratory stimulus to the patient's neck area, mechanoreceptors in the skin will be activated providing feedback to the brain stem and brain to assist with triggering voluntary initiation of swallowing, speech or voice. At greater vibration amplitudes, mechanical stimulation induces movement of the thyroid cartilage and of the extrinsic and intrinsic laryngeal muscles in the region including: the platysma, the sternohyoid, the sternothyroid, the thyrohyoid, cricothyroid and the thyroarytenoid muscles. Some of these muscles contain muscle spindles. The muscle spindle afferents can provide sensory feedback to the central nervous system to assist with triggering voluntary initiation of the muscles for swallowing, speech and voice initiation.

In one embodiment, the stimulation is asserted immediately before a volitional attempt to move or carry out the physiological impaired function, such as swallowing or speaking. In an embodiment, the stimulation comprises an onset period in which the stimulation is asserted about 1 second to about 10 seconds before, about 0.1 second to about 1 second before, about 0.2 second to about 0.5 second before, or about 0.2 second to about 0.4 second before the volitional attempt. The stimulation may also be asserted at the same time as the volitional attempt. Preferably the stimulation of the affected body part is made via a system or device according to the present disclosure before the volitional attempt.

The sensory modality for stimulation includes but is not limited to vibratory stimulation, pressure stimulation, auditory stimulation, temperature stimulation, visual stimulation, electrical stimulation, olfactory stimulation, taste stimulation, and combinations thereof. The stimulation may be controlled electrically, mechanically, chemically, biologically or by any other method known to the skilled artisan. In an embodiment, the stimulation is vibratory, tactile, pressure, or a combination thereof. In an embodiment, the stimulation is vibro-tactile. In an embodiment, vibration stimulation is combined with another stimulation, such as electrical skin surface stimulation (same timing or different).

Vibratory stimulation desirably is applied at a frequency of about 1 to about 100 Hz, about 5 to about 70 Hz, about 30 to 60 Hz, about 50 to about 60 Hz, about 55 to about 60 Hz, or about 58 to about 60 Hz. In an embodiment, the pressure and/or electrical stimulation desirably is applied at a frequency of about 50, about 51, about 52, about 53, about 54, about 55, about 56, about 57, about 58, about 59, or about 60 Hz. The amplitude of vibration preferably may be, for example, about 1 micron to about 2 mm. Amplitudes of about 100 micron to about 1 mm are useful. In an embodiment, the vibrator produces a sequential wave of pressure across bars (such as 1 to 5 oblong bars) at about 0.5 to about 30 times per second, and more preferably about 2 to about 25 times, more preferably about 5 to about 10 times per second. Desirably the pressures are about 1 psi to about 14 psi with rise times of about 2 ms to about 500 ms and more desirably rise times of about 4 to about 150 ms.

Electrical stimulation, if used, should be applied at a rate of 30 Hz at low levels of less than about 2 mA over a small area of 1 cm$^2$ or 25 mA over a large area (about 10 cm$^2$) or greater, or less if the area is smaller (less than about 10 cm$^2$), such as about 0.01 to about 10 mA, about 0.1 to about 7 mA, about 0.5 to about 5 mA, or about 1-3 mA to assure only sensory stimulation is occurring and not resulting in muscle contraction. Levels that do not exceed about 10 mA, about 7 mA, about 5 mA, about 4 mA, about 3 mA, and more desirably about 2 mA, are particularly useful. In an embodiment, the electrical stimulation comprises biphasic pulses (about 50 to about 300 microsecond pulses for example) of about 1 to about 5 mA of current at about 15 to about 60 Hz. When electrical stimulation is utilized care must be taken to assure that muscle contraction is not occurring as stimulation of muscles in the throat area pull the hyoid downward and interfere with swallowing (Humbert et al., 2006; Ludlow et al., 2007).

In a preferred embodiment applicable to all stimulation types (pressure, vibration, electrical, etc) the amplitude of the stimulation (measured as energy output or more directly as electrical current or vibration displacement etc) and/or the rate of the stimulation pulse increases during the swallowing activity. In another embodiment the duration of stimulation is set to the average measured, or expected duration of the patient's swallow. In another embodiment, the stimulation lasts as long as the swallow is perceived to occur, or as long as a switch is activated. However, to prevent central adaptation to the stimulation, the stimulation will only be turned on by the patient when swallowing and will remain off when the patient is not swallowing.

As disclosed herein, the patient that can activate a system or device of the invention stimulates their throat over the larynx thereby eliciting reflex swallowing. In an embodiment, the stimulation is vibratory, tactile, pressure, or a combination thereof In an embodiment, the stimulation is vibrotactile. In an embodiment, the patient controls the stimulation via an actuator communicatively connected to the stimulator. The vibrotactile stimulate of the system and methods of the present invention provides substitute sensation to assist with eliciting swallowing while training the patient to volitionally control swallowing to substitute for their loss of reflexive swallowing. A system according to the present invention, can train the patient to press a button, switch or other equivalent actuator communicatively connected to the stimulator immediately before wanting to swallow thereby providing an alternate sensory input via vibrotactile stimulation (or other similar sensory modalities) to the throat area to enhance volitional control of swallowing of saliva.

The swallowing retraining systems and methods of the present disclosure provides patients and their caregivers the opportunity to practice volitional swallowing early in the post extubation period. FIG. 2 illustrates the neural circuitry in using hand control 203 to trigger volitional swallowing 204 along with simultaneous sensory stimulation 201 which goes to the cortex 202. This is implemented after button press training described above with respect to FIG. 1. Elicitation of the swallowing reflex and safety in swallowing is dependent upon sensory feedback 201 to the brain from sensory mechanoreceptors in the upper airway. If sensory input is withdrawn, persons feel that they can no longer swallow and are at significant increase of aspiration during swallowing (Jafari et al., 2003). The neural circuitry enhances cortical motor control 202 of swallowing coincident with substitution of sensory input 203 from stimulation of the throat area to trigger brain stem circuitry to trigger reflexive swallowing 204 simultaneous with volitional swallowing. By practicing motor onset with a device that provides an alternative sensory input to the brain, such as vibrotactile stimulation, the patient can regain volitional swallowing control readying them to swallow safely first with their own saliva and later to ingest small amounts of food in a controlled volitional fashion. By providing volitional control over swallowing the patient can substitute voluntary swallowing for their loss of reflexive swallowing.

The automatic timer of the systems and devices of the inventions can be used to stimulate the initiation of swallowing on a regular basis to prevent drooling and/or aspiration of the patient's own secretions. In such a configuration, a device of the invention is not dependent upon manual activation by the patient and can be set to initiate swallowing without a user input at a predetermined or variable interval. For example, the automatic timer can be configured to initiate swallowing of saliva to prevent aspiration of secretions from drooling during sleeping. Methods for automatically stimulating swallowing on a regular basis or set interval generally comprise applying a device of the invention to an outside surface of the subject's neck substantially over the subject's larynx and configuring an automatic timer to activate the vibrotactile stimulator to induce the swallowing reflex. In an embodiment, activation of the vibrotactile stimulator produces vibrations at a frequency of about 40 Hz to about 70 Hz and applies pressure of about 1 psi to about 14 psi to the subject's neck during an onset period. In an embodiment, the onset period comprises about 10 ms to about 1.5 s, about 50 ms to about 750 ms, or about 100 ms to about 500 ms. In an embodiment, an automatic timer of the device of the invention is configured to activate the vibrotactile stimulator at an interval of about 1 to about 5 minutes.

In one embodiment, an automatic timer is configured to activate the vibrotactile stimulator once every 3 minutes to about once every 30 minutes for a durations of about 10 ms to about 20 s during which pulsed stimulation is produced at vibrations of about 1 to 300 Hz lasting about 200 ms to about 10 s to induce the swallowing reflex, wherein activation of the vibrotactile stimulator is pulsed at a particular rate and lasts for a particular interval produces vibrations at a frequency of about 40 Hz to about 70 Hz and applies pressure of about 1 psi to about 14 psi to the subject's neck during an onset period.

A device according to the present disclosure can be configured with a counter and timer system to aid in monitoring a patient's use of the device. For example, the counter and timer system can be used to determine or measure frequency of use including how often the patient uses the device, which mode the patient uses, how long and when the device is stimulated, and the like. The data generated by the counter and timer system can be used, for example, to determine compliance with a training or therapy regime. Such data can be used to modify a treatment or training program and/or can alert caretakers to a risk of drooling or aspiration of secretions due to limited use of the system.

Methods for identifying a subject at risk of aspiration from their own secretions generally comprise applying a device of the invention to an outside surface of the subject's neck substantially over the subject's larynx; downloading data from the vibrotactile stimulator after a period of use of the device by the subject; and analyzing to data to determine if the subject is at risk of aspiration from their own secretions due to limited use. The subject activates the device to induce volitional swallowing and the device records the data to allow a health professional to determine if the subject is at risk, due to limited use.

Methods for monitoring patient compliance with a training or therapy regime generally comprise applying a device of claim 1 to an outside surface of the patient's neck substantially over the patient's larynx, wherein the patient activates the device to induce volitional swallowing; downloading data from the vibrotactile stimulator after a period of use of the device by the patient; and analyzing to data to determine the patient's compliance with the training or therapy regime.

For dysphagia treatment, a band may be wrapped around the neck, with an inflatable balloon(s) positioned over the larynx. Upon activation (e.g. by a switch, such as a button) by the user (one who wears the device, or under orders from the wearer) the balloon inflates and puts pressure on the larynx. A controller box is contemplated that may be set to the stimulus type, the stimulus rate (set or increasing) and amplitude (set or increasing) parameters and whether the duration would be set or stay for 2 to 6 seconds or as long as the button is pressed. In an embodiment, the device that stimulates the substitute site is a pressure applying device that attaches to the body by, for example, a Velcro, strap, rubber band, belt, bandage, garment, ace bandage, wire, string, piezoelectric band or film, and/or combination of these or by any other method known in the art.

For instance, the stimulating device may include a contact pressure builder such as a balloon, inflatable tube that inflates to a desired pressure or volume. The art of blood pressure monitors includes devices and methods that may be used as part of the device of the present invention. Preferably a neck wrap is used that positions the pressure applying device to the throat area above the larynx and is adjustable via VELCRO® or any other adjustment means. A small point such as an area as small as about 0.02 square centimeter on the throat over the larynx may be pressed, although larger areas of, for example, about 0.1 to about 10 $cm^2$, about 0.25, to about 5 $cm^2$, about 0.5 to about 2.5 $cm^2$ areas may be used. A desirable area is a 2 cm circle. In a preferred embodiment, at least about 25%, about 35%, about 50%, about 75%, about 85%, about 90%, about 98% or more of the total pressure (calculated as an integrated sum measurement of pressure times surface area) is placed on the throat over the larynx cartilage and not over surrounding muscle. In another embodiment, such selective pressure is achieved, to obtain satisfactory results. In another embodiment, vibratory energy similarly is selectively confined on the throat over the larynx versus the surrounding muscle. In some embodiment, less than about 50%, about 25, about 10%, about 5% or even less pressure is applied to neck muscles. In some embodiments, the stimulation may be cold, vibration, heat, and/or low levels of electrical stimulation capable of inducing a sensory stimulus but not high enough to induce muscle contraction, that condition or disorders or a combination thereof.

Figure 3:
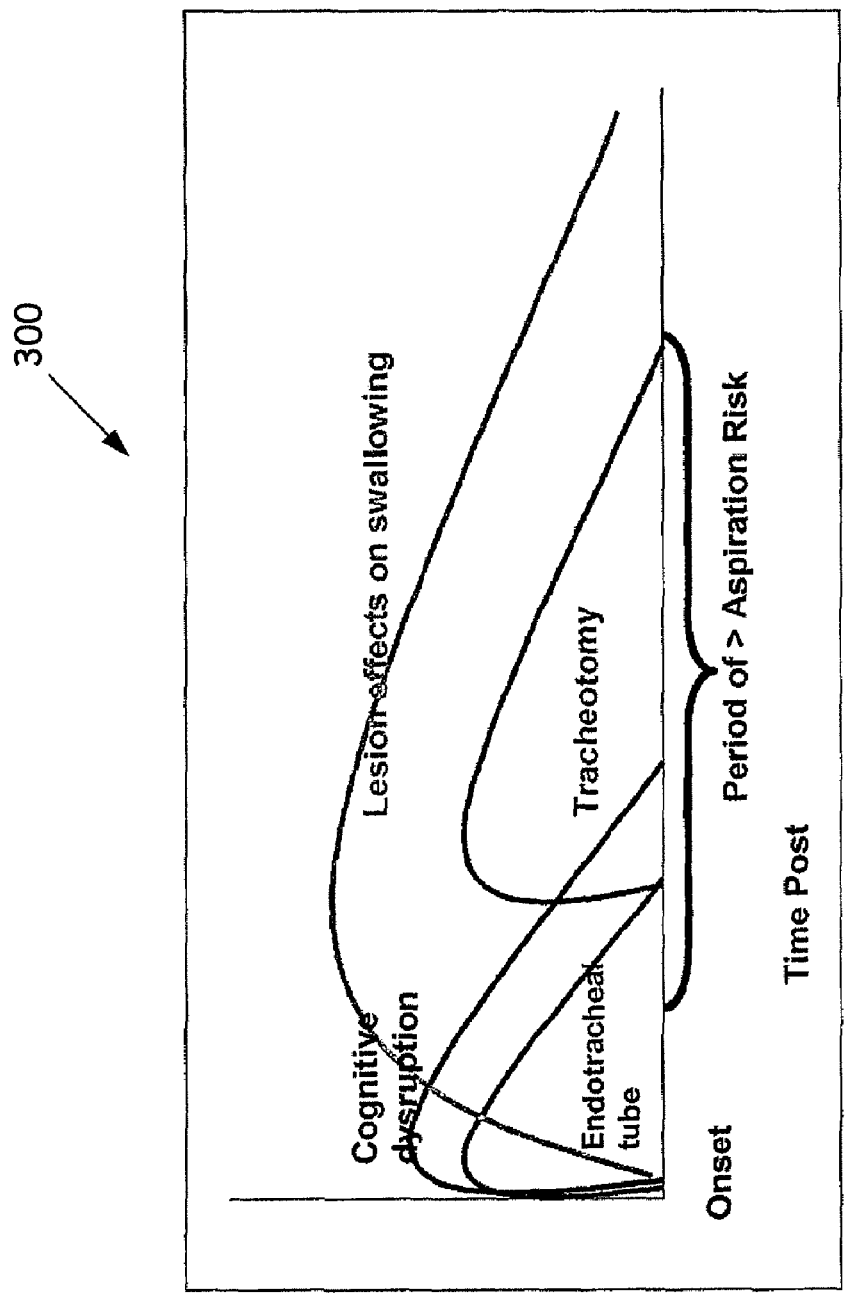
FIG. 3 is a graph depicting conceptualization of events post brain injury.

The systems and devices of the present disclosure can be used in methods for treating impairment of reflexive swallowing due to intubation. Many patients are intubated to maintain the airway for ventilation, including following loss of consciousness due to brain injury or stroke or following coronary artery bypass graft. As the patient recovers cognitive function, extubation of the endotracheal tube occurs. At this point it has been found that the swallowing reflex is reduced (de Larminat, Montravers, Dureuil, & Desmonts, 1995). FIG. 3 shows a conceptualization 300 of events post brain injury, placing patients at high risk of aspiration post extubation with tracheotomy due to reduced afferent stimulation in the upper airway and restricted oral intake, limiting return of reflexive swallowing.

There are most likely several factors contributing reduced swallowing reflex associated with intubation. First, sensory feedback from the upper airway to the brain is reduced due to changes in the sensory function of the mucosa in the upper airway possibly as a result of injury to the mucosa by the endotracheal tube, and sensory organs of nerve endings supplying those organs due to the pressure of the endotracheal tube on the mucosa or resultant edema in the upper airway. In some patients tissue granulation/ulceration occurs when the endotracheal tube has been in place for prolonged periods (over one week). Upon extubation such patients often receive a tracheostomy to provide an adequate airway. It has been shown that during this period following extubation that the normal swallowing reflex is reduced in patients increasing their risk of aspiration of their own saliva (de Larminat, Montravers, Dureuil, & Desmonts, 1995).

In addition to loss of the swallowing reflex, when such patients have a tracheotomy, their sensory input to the upper airway is further reduced because of a lack of air flow through the hypopharynx. In addition, such patients are often placed on a restricted oral intake to prevent aspiration. As a result of their "nothing per oral" (NPO) status, such patients are not swallowing and may be fed through a nasogastric tube or long-term by enteric means for several days or weeks. All of these factors reduce reflexive swallowing. During this period, the methods of the invention can enhance volitional swallowing.

The present invention can provide volitional control for patients with motor control disorders affecting speech and voice. Persons who stutter usually have difficulty with speech initiation and have speech "blocks" when the patient undergoes a loss of volitional control over the laryngeal muscles in particular. This loss of volitional control is manifested as delay in voluntary initiation of muscle contraction or vocal fold movement or an interference due to chronic laryngeal muscle contractions or sustained vocal fold closure. Several studies have suggested that adults who stutter may have increased thresholds to kinesthetic or vibratory stimulation during speech (De Nil & Abbs, 1991). The device and methods of the present invention can enhance vibratory sensory input to persons who stutter. Recent research has shown that persons who stutter have delays in their onset of vocal fold vibration during speech. The present invention increases vibrotactile input to the central nervous system in persons who stutter thereby enhancing their volitional control for speech. When a mechanical displacement is applied to the larynx according to the methods of the invention, it stimulates proprioceptors in the strap muscles, producing a reflexive sternothyroid muscle contraction (Loucks et al., 2005). Because extrinsic laryngeal muscles have a high muscle spindle density, stretch or vibratory stimuli applied to the larynx will serve to enhance muscle activity in this region.

The present invention can provide enhanced volitional control for patients with Spasmodic Dysphonia and Laryngeal Dystonia. Spasmodic dysphonia is a laryngeal focal dystonia, which produces voice abnormalities during speech similar to stuttering. These patients have particular difficulties initiating voicing during speech (Bielamowicz & Ludlow, 2000; C. L. Ludlow, Baker, Naunton, & Hallett, 1988; C. L. Ludlow & Connor, 1987; C. L. Ludlow, Hallett, Sedory, Fujita, & Naunton, 1990) and are often slow to initiate laryngeal muscle activity and have problems maintaining vocal fold vibration during speech. Many focal dystonias have associated sensory abnormalities, with reduced cortical responses in the somatosensory area (Bara-Jimenez, Catalan, Hallett, & Gerloff, 1998; Bara-Jimenez, Shelton, Sanger, & Hallett, 2000) including spasmodic dysphonia (Haslinger et al., 2005). By providing increased vibratory stimulation to the laryngeal area according to the methods of the invention, input to the cortical somatosensory region will enhance volitional voice control for speech in persons with spasmodic dysphonia.

In prior methods for treating stuttering, many devices have been developed to provide altered auditory input, auditory masking or delayed or frequency altered feedback of the speaker's speech to them. Examples include the Edinburgh Masker, Delayed Auditory Feedback by Phonic Ear, Pacemaster, the Casa Futura System, the Vocaltech, the Fluency Master®, and SpeechEasy®. The VocalTech® device includes a vibrator applied to the throat of the user. A microphone picks up the user's voice and then provides both an auditory feedback signal and a vibration to the throat to alter feedback during speech.

Various embodiments of the present invention differ both in concept and in function from prior systems in that the patient/user presses a button to initiate vibrotactile stimulation to aid their ability to initiate speech/voice onset. In such embodiments, the vibratory signal is initiated before the patient attempts to initiate speech and will aid in their volitional control of speech initiation. The VocalTech® device for example only detects speech after it has started and can only be triggered by the patient/user's own speech. The VocalTech® device utilizes a feedback of the patient/user's speech and no other inputs. Therefore if the patient is unable to initiate speech and/or voice, the vibratory signal cannot be initiated. The lack of initiation of the vibratory signal is further exacerbated as there is a delay between the onset of the patient's speech and the onset of the vibratory and auditory feedback. Therefore the VocalTech® device is unable to enhance the patient's ability to onset speech as it is dependent upon the speaker being able to initiate speech. In contrast, the device and the system of the present disclosure assists patients with speech initiation as the vibratory stimulus precedes the person's speech initiation by enhancing mechanical sensory input to cortical control centers for speech. Other auditory masking or delayed or frequency altered feedback devices such as SpeechEasy® also alter or delay the speaker's acoustic speech signal and also require that the speaker is able to initiate speech before the feedback can occur. Therefore these other devices differ both in concept and function from the present invention.

In one embodiment, the present invention is a portable device that can be supplied to adults who stutter and persons with dysphonia to provide stimulation before speech to enhance triggering and controlling voice onset and maintenance for speech. The device of the present disclosure can be used in everyday speaking situations. Patients could purchase the device to use in everyday life to enhance volitional control while speaking.

C. Kits

The present disclosure also relates to kits that include at least one stimulating device of the present disclosure, a container for the device, and instructions for using the device. In an embodiment, the kit comprises a device of the invention that is adapted to be placed in contact with an affected body part, such as the larynx, a container for the device, a switch activated by a patient, and instructions for using the device. The instructions desirably include at least one instruction corresponding to one or more method steps disclosed herein. In an embodiment, a power supply such as a battery is contained within the stimulating device. In an embodiment, disposable covers are included that cover the stimulator during use. In an embodiment the stimulating device includes at least one pump that increases pressure within a chamber such as balloon(s) or tube(s). The device further may include a pressure, stretch, volume, power or other sensor to monitor pressure exerted by the device. In an embodiment the device further includes a switch for setting the amount of desired pressure or movement and/or low levels of electrical stimulation on the skin to increase sensation in the skin in the region overlying the larynx. Switches also may exist for setting frequency and or amplitude of the stimulation.

EXAMPLE

The present disclosure may be better understood with reference to the following example. This example is intended to further illustrate the invention and its underlying principles but is not intended to limit the scope of the invention. Various modifications and changes may be made to the embodiments described above without departing from the true spirit and scope of the disclosure.

Example 1

This example demonstrates that low levels of sensory stimulation to the throat area in patients with severe chronic pharyngeal dysphagia enhances their ability to swallowing safely while high levels of electrical stimulation that activate throat muscles do not enhance swallowing in these patients.

Although surface electrical stimulation has received increased attention as an adjunct to swallowing therapy in dysphagia in recent years (Freed, Freed, Chatburn, & Christian, 2001; Leelamanit, Limsakul, & Geater, 2002; Park, O'Neill, & Martin, 1997; Power et al., 2004), little is known about the effects of transcutaneous stimulation on swallowing physiology. It has been hypothesized that electrical stimulation may assist swallowing either by augmenting hyo-laryngeal elevation (Freed, Freed, Chatburn, & Christian, 2001; Leelamanit, Limsakul, & Geater, 2002) or by increasing sensory input to the central nervous system to enhance the elicitation of swallowing (Park, O'Neill, & Martin, 1997; Power et al., 2004).

When electrical stimulation is applied to the skin or oral mucosa at low current levels it activates the sensory nerve endings in the surface layers providing sensory feedback to the central nervous system. With increased current amplitude, the electric field may depolarize nerve endings in muscles lying beneath the skin surface (Loeb & Gans, 1986) and may spread with diminishing density to produce muscle contraction.

When electrodes are placed in the submental region, therefore, the current density is greatest at the skin surface, and diminishes with depth through the platysma underlying the skin and subcutaneous fat (Sobotta, 1990). Accordingly, as the current is increased in amplitude, increasingly deeper muscles may be recruited, albeit with less efficiency. Such muscles include the anterior belly of the digastric, which can either lower the mandible or pull the hyoid upward depending upon whether the mouth is held closed. Deeper still are the mylohyoid and geniohyoid muscles, which pull the hyoid bone upward and toward the mandible, respectively. These muscles are much less likely to be activated by surface stimulation, however, because of their greater depth.

Similarly when electrodes are placed on the skin overlying the thyroid cartilage in the neck, the current will be greater at the skin with less intensity to the underlying platysma muscle with further reduction to the underlying sternohyoid and omohyoid muscles (Sobotta, 1990), which pull the hyoid downward and backward towards the sternum. The electrical field strength would be even further diminished if it reaches the deeper thyrohyoid muscle, which brings the larynx and hyoid together and the sternothyroid muscle, which lowers the larynx towards the sternum. Given that the sternohyoid muscle is larger and overlies the thyrohyoid and stemothyroid, we previously found that high levels of surface electrical stimulation on the neck could pull the hyoid downward interfering with the ability of normal volunteers to raise the larynx toward the hyoid bone as occurs in normal swallowing (Humbert et al., 2006). In fact, in some healthy volunteers high intensity surface electrical stimulation reduced swallowing safety as it allowed liquid to enter the vestibule (Humbert et al., 2006).

In VitalStim® Therapy (Wijting & Freed, 2003) electrodes are simultaneously activated over the submental and laryngeal regions on the throat, with the aim of producing a simultaneous contraction of the mylohyoid in the submental region (to elevate the hyoid bone) and the thyrohyoid in the neck (to elevate the larynx to the hyoid bone). However, because these muscles lie deep beneath the anterior belly of the digastric, sternohyoid and omohyoid muscles, we hypothesized that simultaneous transcutaneous stimulation with two pairs of electrodes at rest would cause: 1) the hyoid bone to descend in the neck (due to sternohyoid muscle action); 2) the hyoid bone to move posteriorly (due to the omohyoid muscle activity); and, 3) the larynx to descend (if current activates either the sternohyoid or stenothyroid muscles). Further, we hypothesized that in severe chronic dysphagia: 4) when the same array is used at low levels of stimulation just above the sensory threshold, sufficient for sensation but without muscle activation, patients' swallowing might improve due to sensory facilitation; while 5) at higher levels required for motor stimulation, the descent of the hyoid might interfere with swallowing causing increased penetration and aspiration.

Methods

Participant selection criteria included: chronic stable pharyngeal dysphagia, at risk for aspiration for 6 months or more, a score of 21 or greater on the Mini-Mental State Examination (Folstein, Folstein, & McHugh, 1975), a severely restricted diet and/or receiving nutrition through enteric feeding, and medically stable at the time of the study. To be included for study, all participants had to demonstrate a risk of aspiration for liquids on videofluoroscopy during the screening portion of the study.

Procedures

Figure 16:
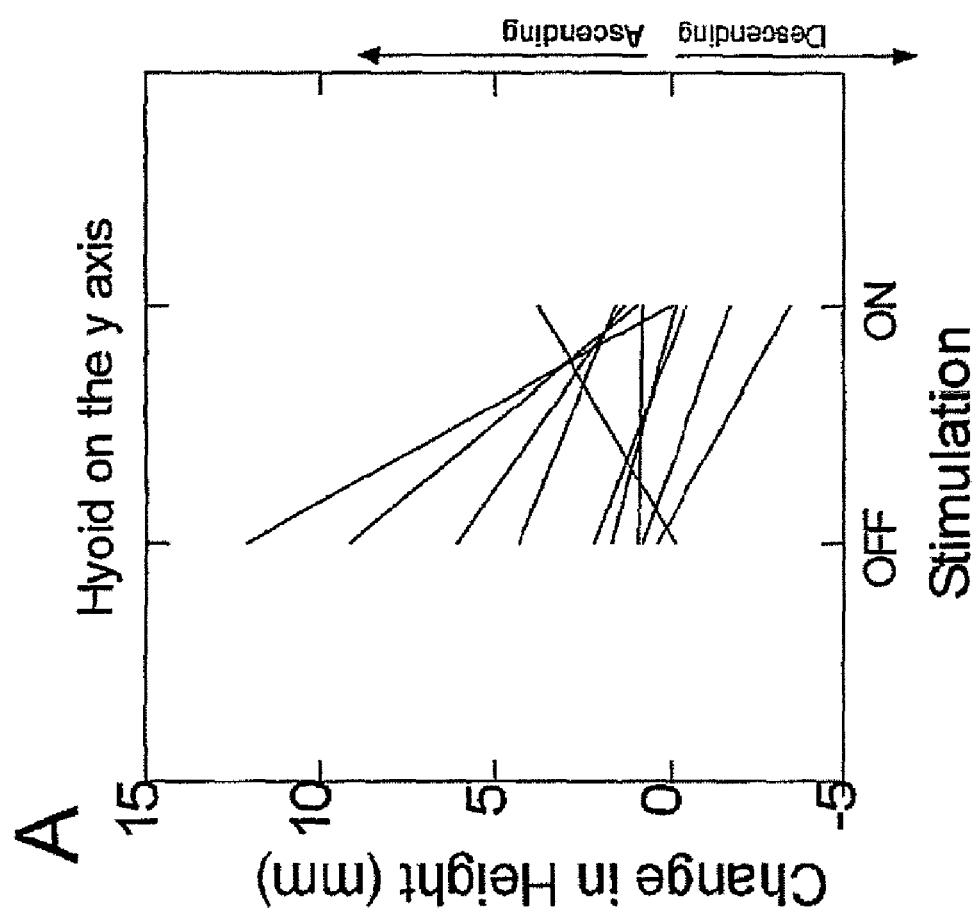
FIG. 16 shows post training mean values for each participant during off and on stimulation conditions. Lowering of the hyoid position on the y axis in the neck is shown with high levels of electrical stimulation on the neck.

Participants were administered informed consent, and had to correctly answer 10 questions to demonstrate that they understood the content of the consent before participating. VitalStim® electrodes (Chattanooga Group, Hixson, Tenn., #59000) and the VitalStim® Dual Channel Unit were used for the study. Two sets of electrodes were used; the top set was placed horizontally in the submental region over the region of the mylohyoid muscle above the hyoid bone (FIG. 16). The bottom set was placed on the skin over the thyroid cartilage on either side of the midline over the region of the thyrohyoid muscle medial to the sternocleidomastoid muscle. This electrode array was recommended as effective during certification training of the first two authors (Wijting & Freed, 2003). A ball bearing with a diameter of 19 mm was taped to the side of the neck for measurement calibration.

After familiarizing the participant with the device, the sensory threshold, which was the lowest current level at which the participant reported a "tingling" sensation on the skin, was identified. Stimulation at the sensory threshold level did not produce movement on videofluoroscopic recordings and was the lowest level at which participants sensed the stimulation on the skin. Movement was first observed when participants first reported a "tugging" sensation, usually around 7 or 8 mA. The maximum motor level was the highest current level a participant could tolerate without discomfort during stimulation on the neck. The sensory and motor levels independently for each set of electrodes was determined. The VitalStim® device cycles automatically from "on" to "off" to "on" again for 1 second every minute. Because the change in stimulation is ramped, this cycling process takes up to 4 s. For the stimulation at rest trials, the participant was told to keep their teeth clenched to prevent jaw opening and the stimulation was simultaneously set at the maximum tolerated levels for both sets of electrodes. When the stimulation duration reached 55 s, videofluoroscopy was turned on and we recorded the fluoroscopic image on S-VHS videotape while the participant was in the resting position and the device automatically cycled from "on", to "off" and then "on" again. The examiner pressed a button at the time of stimulation offset to place a visible marker on the videotape.

During the videofluoroscopic screening examination, we determined which volume, either a 5 or 10 ml of liquid barium bolus, was more challenging and put a participant at risk of aspiration for use during testing. During testing, between one and three swallows were recorded in each of the following conditions in random order: 1) with no stimulation, 2) with both electrode sets on at the sensory threshold level and 3) with both sets at the maximum tolerated stimulation level. Stimulation remained on before, during and after the stimulated swallows. The videotaped recordings included an auditory channel for documentation and a frame counter display for identifying when stimulation changed.

Because radiation exposure during this study was administered for research purposes only and was not for necessary medical care, the Radiation Safety Committee limited us to a short exposure time per participant for the total study. Therefore, depending on radiation exposure time in each part of the study, we were only able to conduct between one and three trials per condition in addition to stimulation at rest for each of the participants.

Movement Analysis

The video of each trial was captured off-line using Peak Motus 8, a 2D motion measurement system (ViconPeak, Centennial, Colo. 80112). The system was equipped with a video capture board at −60 fields/s (−30 frames/s) and a frame size of 608×456 pixels. The radius of the ball bearing (9.5 mm) was used for all measurement calibrations in the horizontal and vertical directions. An investigator used a cursor to identify the points on the most anterior-inferior corner of the second and fourth vertebra on each video frame and a straight line was drawn between these two points to define the y axis. When either the second or fourth vertebra was not visible, the bottom anterior-inferior corner of the first and third vertebrae were used in the same fashion. A line perpendicular to the y axis at the anterior-inferior corner of the lower vertebra served as the x axis. The x and y coordinates for all points were determined in mm relative to the anterior-inferior corner of the second vertebra serving as the origin with anterior and superior points being positive and posterior and inferior points being negative for direction of movement of the hyoid. Four points were marked for each frame, the anterior-inferior points of the two interspersed vertebrae, the anterior inferior point of the hyoid bone and the most posterior and superior point in the subglottal air column (to track the position of the larynx).

The time series plots of the x and y points of the hyoid bone and the y coordinate of the larynx were exported from Peak Modus into Microsoft Excel and then into Systat 11 (Systat Software, Inc., Richmond, Calif.) for analysis. The frame when the stimulation cycled from "on" to "off" was added to the file and used to sort measures into stimulation "on" and stimulation "off. All of the position data were then corrected to place the starting position at zero on both the x and y axes for each subject and then the mean hyoid (x,y) and larynx (y) positions were computed for the stimulation "on" and stimulation "off" conditions for each subject.

Dysphagia Ratings

Four experienced certified speech pathologists initially examined the screening videotapes of randomly selected subjects to decide on a rating system. After assessing several swallows with the Rosenbek Penetration-Aspiration Scale (Rosenbek, Robbins, Roecker, Coyle, & Wood, 1996)(Pen-Asp) it was noted that many of the participants who were on enteric feeding because of their risk of aspiration could score within the normal range, a score of 1 on this scale. This occurred when no penetration or aspiration occurred even though there was severe residual pooling in the pyriform sinuses and none of the bolus entered the esophagus. These participants regurgitated any residual material back into the mouth after a trial, not swallowing any of the liquid but scoring as normal because no material entered the airway. Because scores of 1 on the Pen-Asp scale were at ceiling (normal) and would not allow measurement of improvement, this scale could only measure a worsening in swallowing in these patients. Therefore, another scale was developed that did not have a ceiling effect.

The NIH Swallowing Safety Scale (SSS) captured the abnormalities seen in this patient group, which involved pooling and a lack of esophageal entry with and without penetration and aspiration. When scoring a swallow, a score of 1 was assigned for the occurrence of each the following abnormalities: pooling in the vallecula, penetration into the vestibule from the hypopharynx, pooling in the pyriform, and back up penetration from the pyriform into the laryngeal vestibule. The amount of the bolus material entering and clearing from the upper esophagus was rated as 3 if none entered, 2 if a minimal amount entered, 1 if a moderate amount entered and 0 if all of the bolus was cleared through the upper esophagus. In addition, the total number of aspirations in each swallowing sample were counted. Only normal swallows received a total of 0 on this scale and the maximum score could reach as high as 13 depending upon the number of aspirations or other abnormalities in bolus flow that occurred in a single swallow.

All four speech pathologists viewed each videofluoroscopic recording without knowledge of condition and came to a consensus on all noted behaviors and the Pen-Asp rating before assigning the scores. After repeating ratings on 21 trials to establish reliability, differences in ratings of the same swallow were noted and a set of uniform rules were developed to be followed in assigning scores. These rules were subsequently used to assign ratings to each of the trials in this study. Another set of 18 trials was then repeated to determine the measurement reliability.

Statistical Analyses

To determine the reliability of the position measures, two examiners measured the position for the hyoid on the x and y axes and larynx on the y axis on each frame and then computed means for each during both the stimulated and non-stimulated conditions on 4 of the 10 subjects. The output of the General Linear Model Systat 11 (Systat Software, Inc., Richmond, Calif.) was used to calculate the mean square differences for the within and between subject factors. The Intraclass Correlation Coefficient (ICC) was computed by taking the mean square difference between subjects and subtracting the mean square difference within subjects and then dividing the result by the sum of the mean square difference between subjects and the mean square difference within subjects (Fleiss, 1999).

To determine the reliability of the ratings made using the Pen-Asp Scale and the NIH-SSS, ICCs were computed between the two sets of ratings on each scale from the first 21 trials that were reanalyzed. To identify the items that were unreliable, Cohen's Kappa was computed for the two sets of ratings of each component item of the NIH-SSS using Systat 11 (Systat Software, Inc., Richmond, Calif.). After developing rules for scoring those items that had low reliability, ICCs were computed on the second set of repeated ratings for both the Pen-Asp Scale and the NIH-SSS.

To address the first hypothesis that the hyoid bone would descend in the neck with maximal levels of stimulation at rest, a one-sample directional t-test was used to test for a lowering of the hyoid bone on the y axis between "off" and "on" stimulation. To address the second hypothesis that the hyoid bone would move posteriorly, a one-sample directional t-test was used to test for a retraction of the hyoid bone on the x axis in the "off" and "on" stimulation conditions within subjects. To determine if the larynx descended during stimulation, a one-sample directional t-test was used to test for a lowering of the subglottal air column between the two conditions.

To determine if swallowing improved due to sensory levels of stimulation, one-sample directional t-tests were used to test participants' mean changes in ratings between non-stimulated swallows and stimulated swallows within participants on the Pen-Asp scale and the NIH-SSS with a Bonferroni corrected p value of 0.05/2=0.025. Finally, to determine if swallowing worsened during maximum levels of motor stimulation, one-sample directional t-tests were used to test participants' mean changes in ratings between non-stimulated swallows and stimulated swallows within participants on the Pen-Asp Scale and the NIH-SSS with a Bonferroni corrected p value of 0.05/2=0.025. Pearson correlation coefficients using a Bonferroni corrected p value of 0.025 for statistical significance were computed between both the participant's mean initial severity on the Pen-Asp scale and the NIH-SSS and changes in mean ratings during the sensory stimulation to determine if participant characteristics predicted the degree of benefit. Similarly, Pearson correlation coefficients were computed between the extent to which the hyoid was pulled down in the neck during stimulation at rest and the change in participants' mean ratings for swallowing on the Pen-Asp scale and the NIH-SSS using a Bonferroni corrected p value of 0.025 for statistical significance.

Results

1. Participants

All 11 participants had chronic long-standing dysphagia (Table 1). Their disorder was either subsequent to a CVA in six (>6 months post), post craniotomy for a benign tumor in two (2 and 4 years post) or post traumatic brain injury in two (2 and 3 years post). Only one patient had a chronic progressive neurological disease, Parkinson disease of >20 years with dysphagia for more than 2 years duration.

Ten of the 11 participants participated in the stimulation at rest trials; one did not because of time constraints. During swallow stimulation trials, one of the participants had severe aspiration on an initial swallowing trial and for safety reasons the study was discontinued for that participant. Therefore, we were able to include ten participants in the motor stimulation swallow trials. Because of time constraints, two of the participants did not participate in the low sensory levels of stimulation, leaving 8 participants in the study.

2. Measurement Reliability

The ICC for the movement of the hyoid bone on the y axis in the on and off stimulation conditions were 0.99 and 0.94 respectively and for hyoid movement on the x axis were 0.94 and 0.87. The ICCs for the larynx on the y axis in the stimulation "on" and "off" positions were 0.58 and 0.66 respectively indicating much less reliability on these measures. Because the movement of the larynx was extremely small, ranging from a mean position of 0.4 mm in the stimulation "on" to 0.18 mm in the "off" condition, measurement variability contributed to the variance on this measure.

3. Movement Induced by Stimulation at Rest

Figure 17:
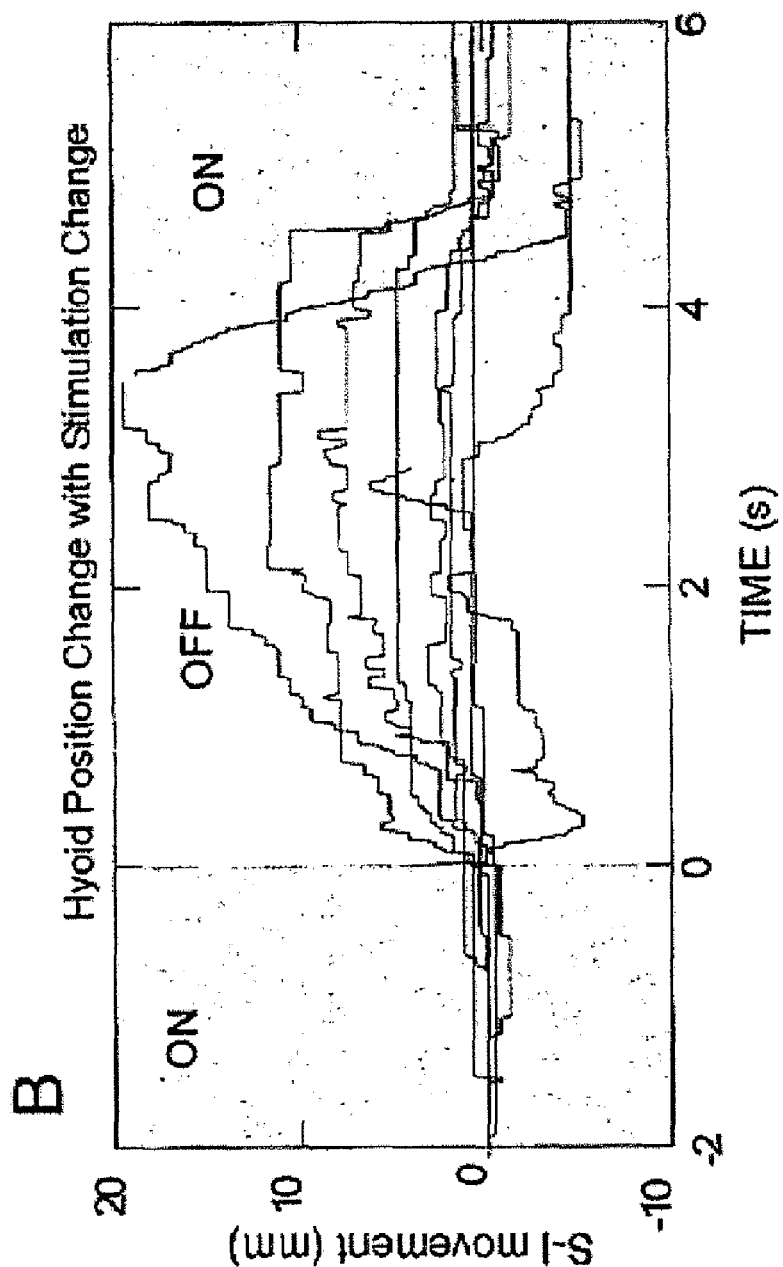
FIG. 17 depicts the traces of hyoid position during high electrical stimulation "on", then stimulation turned "off" followed by stimulation "on" for each of the participants in the study. High levels of electrical stimulation on the throat area lowers the hyoid bone when stimulation is "ON." The hyoid is only able to return to a normal position in the neck when stimulation is "OFF". Because of this action, high motor levels of electrical stimulation interfere with the usual elevation of the hyoid bone which is required for swallowing.

To address the first hypotheses, a one-tailed directional t-test comparing the mean position between "off" and "on" stimulation conditions demonstrated a significant lowering of the hyoid position on the y axis (f=−2.523, o7=9, p=0.016) (see FIG. 16). In FIG. 17 the individual tracings of hyoid movement in each of the patients is shown when the stimulator is turned "on" and then "off" and then "on" again showing elevation of the hydoi bone when the stimulator is turned "off". To address the second hypothesis that the hyoid bone would move posteriorly with stimulation at rest, a directional t-test comparing the mean positions in the "off" and "on" stimulation conditions within subjects was not significant (P=−0.102, αf/=9, p=0.460). Similarly, a directional t-test found no descent in laryngeal position on the y axis during stimulation (£=0.696, d/=9, p=0.748).

4. Reliability of Ratings on the Pen-Asp and NIH SSS

After the first set of 21 repeated ratings, the ICC was 0.965 on the PenAsp scale and 0.764 on the NIH-SSS. Because of concerns about the reliability of the NIH-SSS, we implemented more detailed judging rules for each item where disagreement occurred. A second set of 18 reliability measures using the new judging rules resulted in an ICC for the NIH-SSS that was 0.925, demonstrating adequate reliability when using the scale once the judging rules were developed and implemented.

5. Effects of Low Sensory Stimulation Levels During Swallowing

Figure 18:
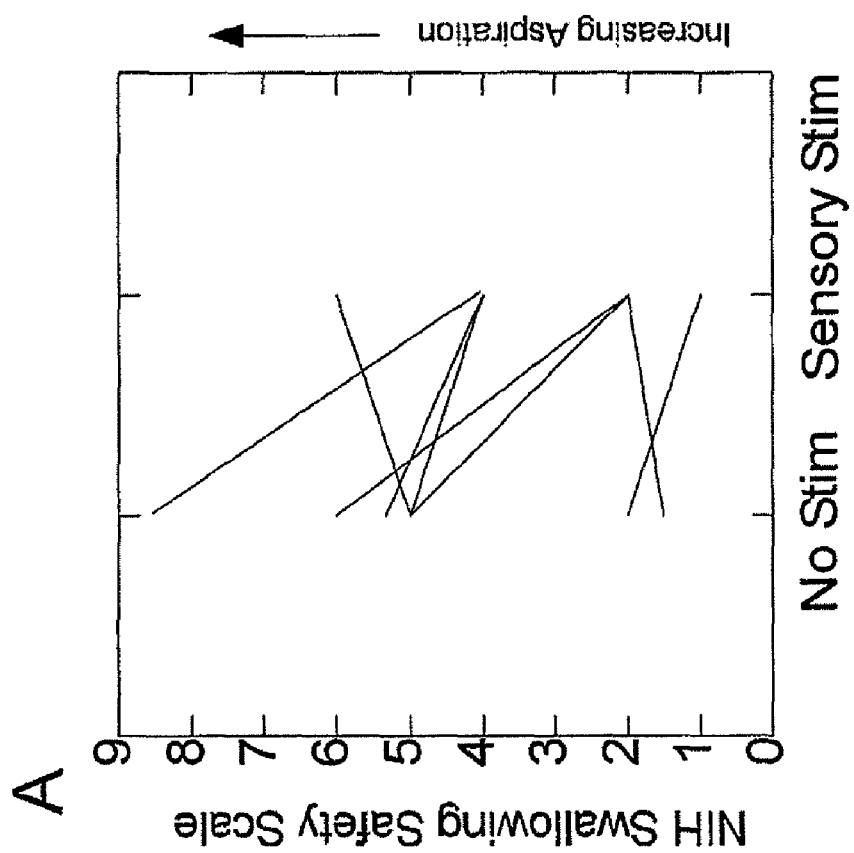
FIG. 18 is a presentation of individual patient reductions in aspiration seen in comparison with swallowing without stimulation versus swallowing with low levels of electrical stimulation at approximately 2 milliamps (mA) applied on the throat. This shows that sensory levels of stimulation enhance swallowing safety.

Due to time constraints only eight of the ten participants completed the sensory condition. To address the fourth hypothesis that swallowing improved with sensory levels of stimulation, one-sample directional t-tests were computed to compare mean change in ratings between non-stimulated swallows and stimulated swallows within participants. The results were not significant on the Pen-Asp Scale (£=0.336, cf/=7, p=0.373) but were significant on the NIH-SSS (.=.2.355, df=7, p=.O25) using a Bonferroni corrected p value of 0.05/2=0.025. This is shown in FIG. 18. Six of the eight of the participants showed a reduction on the NIH-SSS with sensory stimulation during swallowing while five of the eight participants showed a reduction on the Pen-Asp scale.

6. Effects of Motor Stimulation Levels During Swallowing

Figure 19:
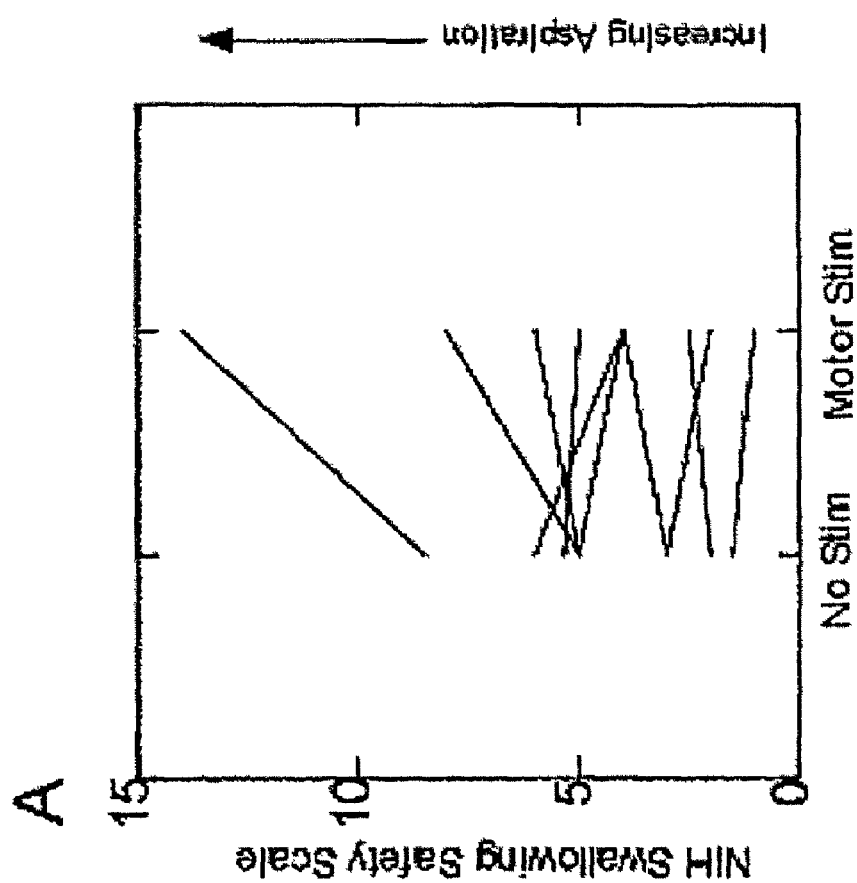
FIG. 19 shows a line graph showing individual participants rating during the stimulated and non-stimulated swallows at motor levels of stimulation on the NIH Swallowing Safety Scale. This graph is auto scaled to the range of the data in the condition. Therefore
Figure 20:
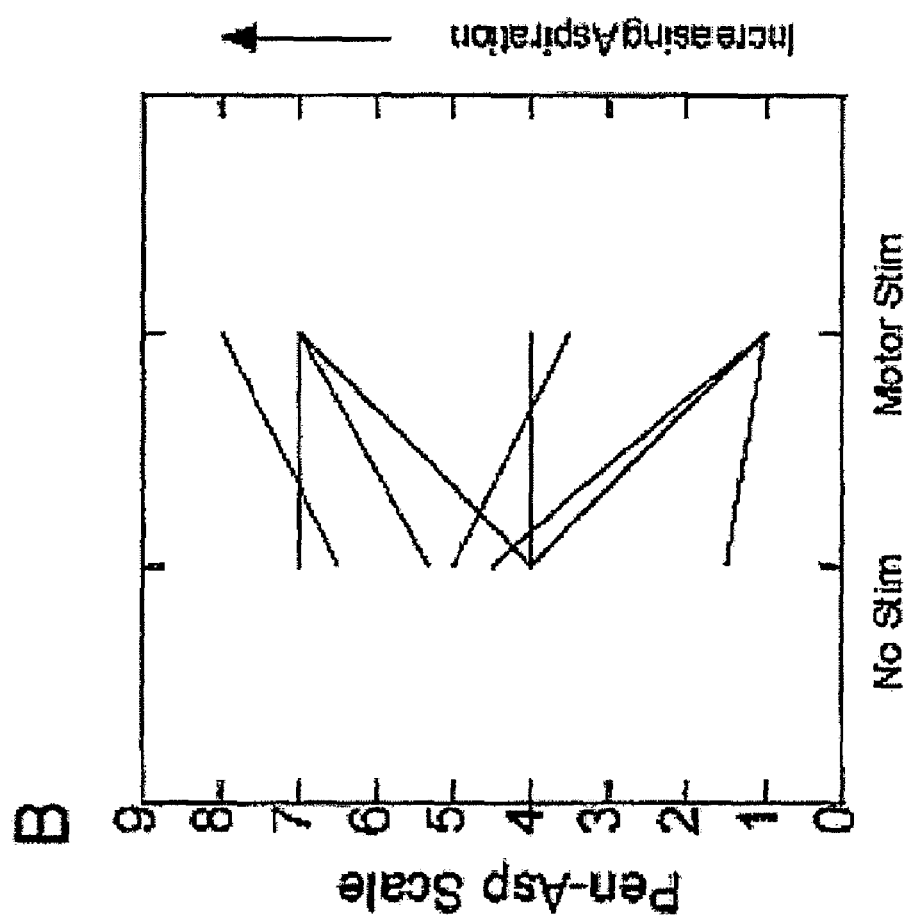
FIG. 20 shows a line graph showing individual participant ratings during stimulated and non-stimulated swallows at motor levels of stimulation on the NIH Penetration-Aspiration scale (Rosenbek et al., 1996).
Figure 21:
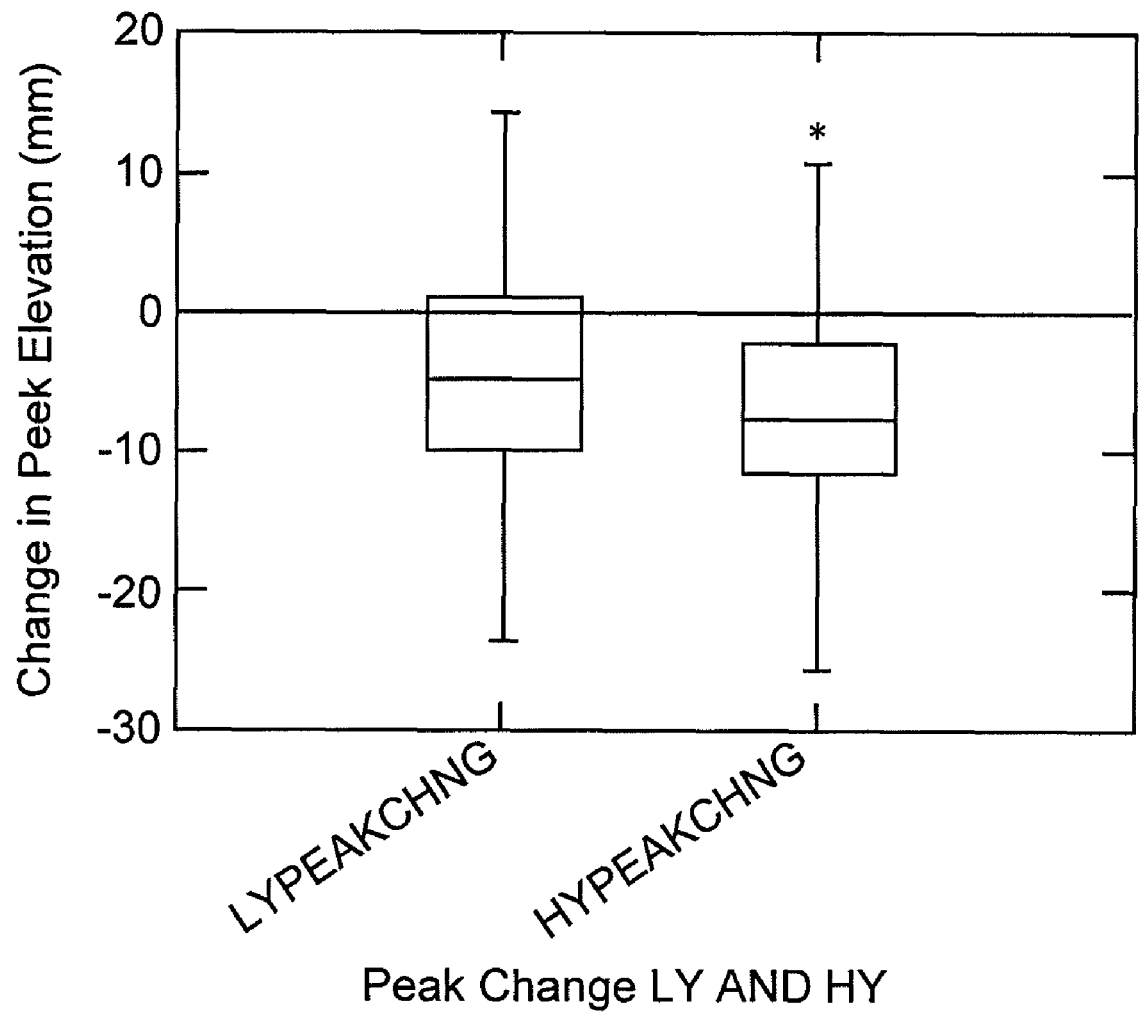
FIG. 21 is a plot of measured peak elevation of the larynx (LYPEAKCHNG) and the peak elevation of the hyoid bone during swallowing (HYPEAKCHNG) in normal volunteers from Humbert et al. (2006) with electrical surface neuromuscular stimulation demonstrating that motor levels of surface electrical stimulation (8 mA or greater) reduce hyolaryngeal elevation during swallowing in healthy adults.

To address the fifth hypothesis that the risk for aspiration and swallowing safety worsened during stimulation, one-sample directional t-tests were computed to examine mean change in ratings between non-stimulated swallows and stimulated swallows within participants. The result was not significant on either the Pen-Asp Scale (/=0.363, d/=9, p=0.637) or on the NIH-SSS (/=−0.881, d/=9, p=0.201) at a Bonferroni corrected p value of 0.05/2=0.025. On the NIH-SSS scale, five of the ten participants had increased risk with motor levels of stimulation (FIG. 19), while on the Pen-Asp equal numbers of participants increased or decreased with motor levels of stimulation (FIG. 20).

7. Relationship Between Severity of Dysphagia and Changes in Swallowing with Stimulation The Pearson correlation coefficient between participants' initial severity on the Pen-Asp scale and change in swallowing with sensory stimulation was not significant ($/=0.142$, $p=0.737$). Similarly, participants' initial severity and change in swallowing with sensory stimulation on the NIH-SSS ($/=0.701$, $p=0.053$) was not significant using a Bonferroni corrected a value of 0.025 for statistical significance. A Pearson correlation coefficient between both the participants' initial severity on the Pen-Asp scale and change in swallowing with motor stimulation was not significant ($/=-0.501$, $p=0.140$), nor was the correlation between participants' initial severity on the NIH-SSS and change in swallowing with motor stimulation ($/=-0.190$, $p=0.599$), using a Bonferroni corrected a value of 0.025 for statistical significance.

8. Relationship of Movement during Stimulation at Rest with Changes in Swallowing with Stimulation Pearson correlation coefficients were computed between the extent to which the hyoid was pulled down in the neck during stimulation at rest and the change in swallowing on the Pen-Asp and the NIH-SSS using a Bonferroni corrected o value of 0.025 for statistical significance. No significant relationship was found between the degree of improvement on the NIH-SSS and the degree to which the hyoid bone was depressed during motor levels of stimulation at rest ($r=-0.388$, $n=9$, $P=0.302$). The improvement in the Pen-Asp scale during motor stimulation was significantly inversely related to the degree to which the hyoid bone was depressed during motor levels of stimulation at rest ($r=-0.828$, $n=9$, $p=0.006$). The relationship demonstrated that those with the greatest hyoid depression at rest had the greatest reduction on the Pen-Asp scale during motor levels of stimulation while swallowing.

Discussion

One purpose of this study was to determine the physiological effects of surface electrical stimulation on the position of the hyoid and larynx in the neck. We had predicted that when both the submental and laryngeal electrode pairs were stimulating at the participants' maximal tolerated levels, that the hyoid bone would be pulled downward, most likely due to stimulation of the sternohyoid muscle. The data supported this hypothesis; all but two of the participants had depression of the hyoid bone by as much as 5 to 10 mm during stimulation at rest (FIGS. 6A and 6B). We also predicted that the hyoid bone might be pulled posteriorly; however, limited anterior-posterior movement occurred in the hyoid bone. Three participants had hyoid anterior movement, by as much as 5 mm in one case, while the others had minimal movement in the posterior direction. Whereas minimal ascending movement (2-3 mm) occurred in the larynx in two participants, none of the other participants experienced any appreciable laryngeal movement (FIG. 6D) and the 2-3 mm changes were potentially due to measurement variation. To summarize these findings, the only appreciable motoric effects of surface electrical stimulation was to cause the hyoid bone to descend in the neck, producing movement in the opposite direction from that required for swallowing.

These results suggest that when surface stimulation was applied to the neck at rest, stimulation was either too weak or not deep enough to stimulate axons innervating the muscles that produce hyoid and laryngeal elevation such as the mylohyoid and the thyrohyoid muscles respectively. No change in laryngeal position was observed with surface stimulation at rest.

Another purpose of this study was to determine the immediate effects of surface stimulation on swallowing in participants with chronic pharyngeal dysphagia. Based on previous use of sensory stimulation in the oral and pharyngeal cavities to augment patients' volitional control of swallowing (Hamdy et al., 2003; Park, O'Neill, & Martin, 1997), we compared sensory levels of electrical stimulation just above the participants' sensory threshold for detecting a tingling sensation on the skin, and found a significant improvement during swallowing on the NIH-SSS scale (FIG. 18). The improvement on the NIH-SSS tended to be related to higher initial scores; that is the more severely affected patients were those who had the greatest improvement with stimulation. Because the NIH-SSS captures pharyngeal pooling and failed esophageal entry in contrast with the Pen-Asp scale, which only measures aspiration and penetration, sensory stimulation may be somewhat helpful in those patients who have reduced ability to clear the bolus from the airway.

Based on the expected lowering of the hyoid with motor levels of stimulation, we hypothesized that the group would have increased penetration and aspiration during swallowing with motor stimulation. No group change in aspiration was noted on either scale with motor levels of stimulation. When the degree of improvement on the Pen-Asp scale with motor levels of stimulation was examined relative to the degree of hyoid depression, we found an unexpected relationship indicating that patients with the greatest hyoid depression during motor levels of stimulation at rest had the greatest improvement during swallowing with the same levels of stimulation. When the hyoid was depressed with stimulation, a patient probably experienced a greater resistance to hyo-laryngeal elevation during swallowing. Perhaps those patients who felt a greater downward pull on the hyoid, when stimulation was turned on at maximal levels, made a greater effort to elevate the hyo-laryngeal complex when swallowing in an attempt to overcome the effects of the stimulation. It could also be the case that those patients who had greater residual power in their hyo-laryngeal muscles would have not only experienced greater hyoid descent with stimulation but could also have greater residual power that they could recruit for hyo-laryngeal elevation to counteract the stimulation induced descent during swallowing.

This study also addressed the immediate physiological effects of the use of surface electrical stimulation at rest and during swallowing. This study suggests that electrical stimulation should be used judiciously dependent upon a patient's type and degree of difficulty with swallowing. In those patients who already have some ability to raise the hyo-laryngeal complex, hyoid depression with stimulation may serve as "resistance" during therapy. On the other hand, if a patient is unable to produce any hyo-laryngeal elevation, and therefore would not be able to resist the hyoid depression induced by stimulation, stimulation might put such a patient at greater risk of aspiration as the hyo-laryngeal complex is held down during swallowing. This may have occurred in some of the more severely affected patients who increased in severity on the Pen-Asp and NIH-SSS with motor levels of stimulation, while those less impaired did not change (FIGS. 19 and 20).

In this study, both submental and laryngeal pairs of electrodes were used simultaneously as is recommended for VitalStim® Therapy. It is likely that the simultaneous stimulation resulted in hyoid lowering because the stronger stimulation to the more superficial and larger sternohyoid and sternothyroid muscles overcame any action that might have been induced by stimulation of the mylohyoid muscle in the submental region or the thyrohyoid muscle beneath the sternohyoid in the throat region. Some have proposed using submental stimulation alone to activate the anterior belly of the digastric and the mylohyoid muscles to pull the hyoid bone upward. However, elevation of the hyoid bone without simultaneous stimulation of the thyrohyoid to raise the larynx would leave the larynx down resulting in further opening of the vestibule and increased risk of aspiration. Only if the mylohyoid and thyrohyoid muscles are activated together, without contraction of the sternohyoid, would both the hyoid and larynx be raised together as has previously been shown with intramuscular stimulation (Burnett, Mann, Cornell, & Ludlow, 2003). This cannot be achieved using surface stimulation, because the larger sternohyoid muscle overlies the thyrohyoid and pulls the hyoid downward.

The finding that the group as a whole improved with sensory levels of stimulation alone on the Pen-Asp scale was unexpected. Previous research has shown that stimulation of the anterior and posterior faucial pillars was most effective stimulation for eliciting a swallow reflex in normal persons (Pommerenke, 1927). Although not studied physiologically, stroking the throat region is known to assist with the spontaneous elicitation of swallowing in infants and some mammals. Stimulation of either the glossopharyngeal or the superior laryngeal nerves has been shown to elicit swallowing in animals (Jean, 1984) and bilateral chemical blockade of the superior laryngeal nerves disrupts swallowing in normal humans (Jafari, Prince, Kim, & Paydarfar, 2003). It has not been observed that sensory stimulation to the surface of the throat would reflexively trigger a swallow in adults; however, sensory levels of electrical stimulation on the skin in the throat may facilitate volitional triggering of swallowing in dysphagia. These results suggest that low levels of electrical stimulation on the skin might be beneficial in some patients. Because such low levels of electrical stimulation were not observed to induce hyoid depression, we posit that none of the patients would be put at increased risk for aspiration using lower sensory levels of stimulation. Before surface electrical stimulation is used, the patients should be carefully screened to determine whether they would be placed at increased risk of aspiration with a procedure that lowers the hyoid.

TABLE 1

Participant Characteristics and Surface Electrical Stimulation levels

| Subject | Sex | Age | Etiology | Time post onset (years) | Status | Sensory Threshold Upper/Lower Electrode (mA) | Motor Threshold Upper/Lower Electrode (mA) |
|---|---|---|---|---|---|---|---|
| 1. | M | 66 | hemmorrhage in veterbrobasilar circulation | 2.5 | PEG, bilateral sensory loss, pooling, previous aspiration pneumonia | 3.5/2.0 | 8.0/8.0 |
| 2. | M | 66 | Parkinson disease | 20 years duration, Severe dysphagia 2+ years | PEG for 2 years, swallowed own secretions Recurrent pneumonias | 6.0/2.5 | 10.0/10.0 |
| 3. | M | 76 | Stroke | 1 | PEG unable to handle secretions Aspiration pneumonia X 3, normal sensation | 4.0/2.0 | 14/7.0 |
| 4. | M | 78 | Brain stem stroke | 5 | PEG, frequent aspiration pneumonias, severe reductions in UES relaxation, normal sensation | 7.0/7.0 | 14/14 |
| 5. | F | 47 | Left occipital and brain stem stroke | 3 | PEG, unable to handle secretions Bilateral sensory loss | 3.0/4.0 | 10/10 |
| 6. | M | 25 | closed brain surgery | 2 | Aspirations on liquids, bilateral sensory loss | 3.5/6.0 | 16.6/13.0 |
| 7. | M | 48 | Cerebellar hemorrhage with carniotomy | 2 | PEG, Unable to handle secretions, aspiration pneumonia, pooling, Normal sensation | 3.0/2.5 | 18.0/18.0 |

TABLE 1-continued

Participant Characteristics and Surface Electrical Stimulation levels

| Subject | Sex | Age | Etiology | Time post onset (years) | Status | Sensory Threshold Upper/Lower Electrode (mA) | Motor Threshold Upper/Lower Electrode (mA) |
|---|---|---|---|---|---|---|---|
| 8. | F | 44 | Subarchnoid hemorrhage left vertebral artery | 2 | Tracheostomy PEG tube Normal sensation bilateral Pooling of secretions | 4.0/2.0 | 12.5/9.5 |
| 9. | M | 45 | Traumatic brain injury | 3 | Chokes on saliva, eats soft foods, drooling, Bilateral sensory loss | 3.0/4.0 | 18.0/16.0 |
| 10. | M | 61 | Left hemisphere stroke | .5 | PEG, Inable to handle secretions, Normal sensation on left, pooling, BOTOX ® in UES | 1.5/4.0 | 13.0/13.0 |
| 11. | M | 47 | Crainotomy for brain stem tumor | 4 | Severe aspiration, multiple aspiration pneumonias Bilateral sensory loss | 1.5/1.5* | 14/18 |

*Couldn't study effects of either sensory or motor stimulation during swallowing due to severe aspiration.

REFERENCES

References not listed specifically can be found in the literature by a search for the authors. U.S. application Ser. No. 10/529,401 entitled Methods and Devices for Intramuscular Stimulation of Upper Airway and Swallowing Muscle Groups filed on Mar. 28, 2005, is incorporated by reference in its entirety. The references found in that patent application are relevant and incorporated by reference with respect to the details of stimulating devices and method which are contemplated for use in embodiments presented here.

All references cited herein are hereby incorporated by reference in their entirety.

Aviv, J. E., Martin, J. H., Sacco, R. L., Zagar, D., Diamond, B., Keen, M. S., et al. (1996). Supraglottic and pharyngeal sensory abnormalities in stroke patients with dysphagia. Ann Otol Rhinol. Laryngol., 105, 92-97.

Aviv, J. E., Sacco, R. L., Mohr, J. P., Thompson, J. L., Levin, B., Sunshine, S., et al. (1997). Laryngopharyngeal sensory testing with modified barium swallow as predictors of aspiration pneumonia after stroke. Laryngoscope, 107, 1254-1260.

Aviv, J. E., Sacco, R. L., Thomson, J., Tandon, R., Diamond, B., Martin, J. H., et al. (1997). Silent laryngopharyngeal sensory deficits after stroke. Ann Otol Rhinol. Laryngol., 106, 87-93.

Bara-Jimenez, W., Catalan, M. J., Hallett, M., & Gerloff, C. (1998). Abnormal somatosensory homunculus in dystonia of the hand. Ann Neurol, 44 {5}, 828-831.

Bara-Jimenez, W., Shelton, P., Sanger, T. D., & Hallett, M. (2000). Sensory discrimination capabilities in patients with focal hand dystonia. Ann Neurol, 47(3), 377-380.

Bielamowicz, S., & Ludlow, C. L. (2000). Effects of botulinum toxin on pathophysiology in spasmodic dysphonia. Ann Otol Rhinol Laryngol, 109, 194-203.

Burnett, T. A., Mann, E. A., Cornell, S. A., & Ludlow, C. L. (2003). Laryngeal elevation achieved by neuromuscular stimulation at rest. J Appl Physiol, 94(1), 128-134.

Burnett, T. A., Mann, E. A., Stoklosa, J. B., & Ludlow, C. L. (2005). Self-triggered functional electrical stimulation during swallowing. J Neurophysiol, 94(6), 4011-4018.

Conforto, A. B., Kaelin-Lang, A., & Cohen, L. G. (2002). Increase in hand muscle strength of stroke patients after somatosensory stimulation. Ann Neurol, 57(1), 122-125.

de Larminat, V., Montravers, P., Dureuil, B., & Desmonts, J. M. (1995). Alteration in swallowing reflex after extubation in intensive care unit patients. Crit Care Med, 23(3), 486-490.

De Nil, L. F., & Abbs, J. H. (1991). Kinaesthetic acuity of stutterers and non-stutterers for oral and non-oral movements. Brain, 114, 2145-2158.

Dick, T. E., Oku, Y., Romaniuk, J. R., & Cherniack, N. S. (1993). Interaction between central pattern generators for breathing and swallowing in the cat. J Physiol, 465, 715-730.

Dubner, R., Sessle, B. J., & Storey, A. T. (1978). The Neural Basis of Oral and Facial Function. New York: Plenum Press.

Fleiss, J. L. (1999). The design and analysis of clinical experiments. New York, N.Y.: John Wiley & Sons, Inc.

Folstein, M. F., Folstein, S. E., & McHugh, P. R. (1975). "Mini-mental state". A practical method for grading the cognitive state of patients for the clinician. J Psychiatr Res, 72(3), 189-198.

Fraser, C, Rothwell, J., Power, M., Hobson, A., Thompson, D., & Hamdy, S. (2003). Differential changes in human pharyngoesophageal motor excitability induced by swallowing, pharyngeal stimulation, and anesthesia. Am J Physiol Gastrointest Liver Physiol, 285(1), G137-144.

Freed, M. L., Freed, L., Chatburn, R. L., & Christian, M. (2001). Electrical stimulation for swallowing disorders caused by stroke. Respir Care, 46(5), 466-474.

Hägg. M & Larsson, B. (2004) Effects of motor and sensory stimulation in stroke patients with long-lasting dysphagia. Dysphagia, 19: 219-230.

Hamdy, S., Jilani, S., Price, V., Parker, C, Hall, N., & Power, M. (2003). Modulation of human swallowing behaviour by thermal and chemical stimulation in health and after brain injury. Neurogastroenterol Motil, 75(1), 69-77.

Haslinger, B, Erhard, P., Dresel, C., Castrop, F., Roettinger, M., Ceballos-Baumann, A O. "Silent event-related" fMRI reveals reduced sensorimotor activation in laryngeal dystonia. Neurology, 65: 1562-15

Holzer SE, and Ludlow, CL. (1996) The swallowing side effects of botulinum toxin type A injection in spasmodic dysphonia. Laryngoscope, 106: 88-92.

Humbert I, Lynch J, Ludlow, CL. Estimating the prevalence of chronic pharyngeal dysphagia in neurological disorders., in preparation 2008.

Humbert I A, Poletto C J, Saxon K G, Kearney P R, Crujido L., Wright-Harp, W., Payne, J., Jeffries, N, Sonies, BC, Ludlow CL. (2006) J. Appl. Physiology 101: 1657-1663

Jafari, S., Prince, R. A., Kim, D. Y., & Paydarfar, D. (2003). Sensory regulation of swallowing and airway protection: a role for the internal superior laryngeal nerve in humans. J Physiol, 550(Pt 1), 287-304.

Jean, A. (1984). Control of the central swallowing program by inputs from the peripheral receptors. A review. J Auton Nerv Syst, 10, 225-233.

Leelamanit, V., Limsakul, C, & Geater, A. (2002). Synchronized electrical stimulation in treating pharyngeal dysphagia. Laryngoscope, 112(12), 2204-2210.

Loeb, G. E., & Gans, C. (1986). Electromyography for Experimentalists. Chicago: The University of Chicago.

Logemann, J. A. (1993). Noninvasive approaches to deglutitive aspiration. Dysphagia, 8(4), 331-333.

Logemann, J. A., Pauloski, B. R., Colangelo, L., Lazarus, C, Fujiu, M., & Kahrilas, P. J. (1995). Effects of a sour bolus on oropharyngeal swallowing measures in patients with neurogenic dysphagia. J Speech Hear Res, 38(3), 556-563.

Logemann, J. A. (1998). Evaluation and treatment of swallowing disorders (2nd ed.). Austin, Tex.: Pro-Ed.

Loucks, T. M., Poletto, C. J., Saxon, K. G., & Ludlow, C. L. (2005). Laryngeal muscle responses to mechanical displacement of the thyroid cartilage in humans. J Appl Physiol, 99(3), 922-930.

Lowell S Y, Poletto C J, Knorr-Chung B R, Reynolds R C, Simonyan K, Ludlow C L (2008). Sensory stimulation activates both motor and sensory components of the swallowing system. NeuroImage, 42: 285-295.

Ludlow, C. L., Baker, M., Naunton, R. F., & Hallett, M. (1988). Intrinsic laryngeal muscle activation in spasmodic dysphonia. In R. Benecke, B. Conrad & C. D. Marsden (Eds.), Motor Disturbances (1 ed., pp. 119-130). Orlando: Academic Press.

Ludlow, C. L., & Connor, N. P. (1987). Dynamic aspects of phonatory control in spasmodic dysphonia. J Speech Hear Res, 30, 197-206.

Ludlow, C. L., Hallett, M., Sedory, S. E., Fujita, M., & Naunton, R. F. (1990). The pathophysiology of spasmodic dysphonia and its modification by botulinum toxin. In A. Berardelli, R. Benecke, M. Manfredi & C. D. Marsden (Eds.), Motor Disturbances (2 ed., pp. 274-288). Orlando: Academic Press.

Ludlow, C. L., Humbert, I. J., Poletto, C. J., Saxon, K. S., Kearney, P. R., Crujido, L., et al. (2005). The Use of Coordination Training for the Onset of Intramuscular Stimulation in Dysphagia, Proceedings of the International Functional Electrical Stimulation Society, 2005.

Ludlow, C. L., Humbert, I. J., Saxon, K. G., Poletto, C. J., Sonies, B. C, & Crujido, L. (2006). Effects of surface stimulation both at rest and during swallowing in chronic pharyngeal dysphagia. Dysphagia, epub, May 23, 2006.

Lundy, D. S., Smith, C, Colangelo, L., Sullivan, P. A., Logemann, J. A., Lazarus, C. L., et al. (1999). Aspiration: cause and implications. Otolaryngol Head Neck Surg, 120{4), 474-478.

Mifflin, S. W. (1997). Intensity and frequency dependence of laryngeal afferent inputs to respiratory hypoglossal motorneurons. J Appl Physiol, 83, 1890-1899.

Nishino, T., Tagaito, Y., & Isono, S. (1996). Cough and other reflexes on irritation of airway mucosa in man. Pulm Pharmacol, 9(5-6), 285-292.

Ootani, S., Umezaki, T., Shin, T., & Murata, Y. (1995). Convergence of afferents from the SLN and GPN in cat medullary swallowing neurons. Brain Res Bull, 37(4), 397-404.

Park, C. L., O'Neill, P. A., & Martin, D. F. (1997). A pilot exploratory study of oral electrical stimulation on swallow function following stroke: an innovative technique. Dysphagia, 72(3), 161-166.

Peurala S H, Pitkanen K, Sivenius J, Tarkka I M. Cutaneous electrical stimulation may enhance sensorimotor recovery in chronic stroke. Clin Rehabil. 2002; 16:709-716).

Pick, N., McDonald, A., Bennett, N., Litsche, M., Dietsche, L., Legerwood, R., et al. (1996). Pulmonary aspiration in a long-term care setting: clinical and laboratory observations and an analysis of risk factors. J Am Geriatr Soc, 44(7), 763-768

Pommerenke, W. T. (1927). A study of the sensory areas eliciting the swallowing reflex. American Journal of Physiology, 84(1), 36-41.

Portens C., Johns M N., Hapner E R (2008). A review of patient adherence to the recommendations for voice therapy. J. Voice., 22: 1892-196.

Power, M., Fraser, C, Hobson, A., Rothwell, J. C, Mistry, S., Nicholson, D. A., et al. (2004). Changes in pharyngeal corticobulbar excitability and swallowing behavior after oral stimulation. Am J Physiol Gastrointest Liver Physiol, 286(1), G45-50.

Power, M. L., Fraser, C. H., Hobson, A., Singh, S., Tyrrell, P., Nicholson, D. A., et al. (2006). Evaluating oral stimulation as a treatment for Dysphagia after stroke. Dysphagia, 21(λ), 49-55.

Robbins, J., Butler S D G, Daniels, S K, Dierz Gross R, Langmore S., Lazarus C L, Martin-Harris B, McCabe D, Musson, Rosenbex, J. (2008) Swallowing and dysphagia rehabilitation: translating principles of neural plasticity into clinically orientated evidence. J Speech Lang. Hear. Res., 51, S276-300.

Rosenbek, J. C, Robbins, J. A., Roecker, E. B., Coyle, J. L., & Wood, J. L. (1996). A penetration-aspiration scale. Dysphagia, 11(2), 93-98.

Sedory-Holzer, S. E., & Ludlow, C. L. (1996). The swallowing side effects of botulinum toxin type A injection in spasmodic dysphonia. Laryngoscope, 106, 86-92.

Setzen, M., Cohen, M. A., Perlman, P. W., Belafsky, P. C, Guss, J., Mattucci, K. F., et al. (2003). The association between laryngopharyngeal sensory deficits, pharyngeal motor function, and the prevalence of aspiration with thin liquids. Otolaryngol Head Neck Surg, 128(1), 99-102.

Sobotta, J. (1990). Sobotta Atlas of Human Anatomy (A. N. Taylor, Trans. 11th English Edition ed. Vol. Volume 1 Head, Neck, Upper limbs, skin). Baltimore-Munich: Urban & Schwarzenberg.

Struppler A, Angerer B, Havel P. Modulation of sensorimotor performances and cognition abilities induced by RPMS: clinical and experimental investigations. Suppl Clin Neurophysiol. 2003; 56:358-367;

Theurer, J. A., Bihari, F., Barr, A. M., & Martin, R. E. (2005). Oropharyngeal stimulation with air-pulse trains increases swallowing frequency in healthy adults. Dysphagia, 20(4), 254-260.

van Dijk K R, Scherder E J, Scheltens P, Sergeant J A. Effects of transcutaneous electrical nerve stimulation (TENS) on non-pain related cognitive and behavioural functioning. Rev Neurosci. 2002; 13:257-270;

Wijting, Y., & Freed, M. L. (2003). VitalStim Therapy Training Manual. Hixson, Tenn.: Chattanooga Group.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A device, comprising:
    a vibrotactile stimulator configured to apply at least one stimulus to the outside surface of a subject's neck, wherein the vibrotactile stimulator comprises:
        a vibrational transducer;
        a manual stimulation module configured to manually engage the vibrational transducer;
        an automatic stimulation module configured to automatically engage the vibrational transducer;
        a manual counter configured to determine the number of times the manual stimulation module is engaged; and
        an automatic counter configured to determine the number of times the automatic stimulation module is engaged;
    a connector configured to attach the vibrotactile stimulator to an outside surface of the subject's neck; and
    a switch control communicatively connected to the vibrotactile stimulator and configured to selectively engage the manual stimulation module or the automatic stimulation module.

2. The device of claim 1, wherein the connector comprises an adjustment mechanism configured to position a contact section substantially over the subject's larynx.

3. The device of claim 2, wherein the adjustment mechanism is configured to shift the position of the contact section within a circle having an area of about 0.1 to about 10 cm$^2$, about 0.25 to about 5 cm$^2$, or about 0.5 to about 2.5 cm$^2$.

4. The device of claim 1, wherein the vibrational transducer is a vibrator motor.

5. The device of claim 1, wherein the automatic stimulation module comprises an automatic timer.

6. The device of claim 1, wherein the manual counter and the automatic counter are configured to be manually interrogated and reset.

7. The device of claim 1, wherein the manual counter and the automatic counter are configured to be remotely interrogated and reset.

8. The device of claim 1, wherein the at least one stimulus comprises a sequential wave of pressure.

9. The device of claim 1, wherein the vibrational transducer produces a wave having an amplitude of about 1 micron to about 2 mm or about 100 microns to about 1 mm.

10. The device of claim 1, wherein the vibrational transducer produces a wave having a frequency of about 50 Hz to about 70 Hz.

11. The device of claim 10, wherein the vibrational transducer produces a wave having a frequency of about 59 Hz.

12. The device of claim 1, wherein the vibrational transducer produces a wave having a rise time of about 25 ms to about 500 ms or about 75 ms to about 150 ms.

13. The device of claim 1, wherein the at least one stimulus comprises a vibrational stimulus, an auditory stimulus, a temperature stimulus, a visual stimulus, an olfactory stimulus, a gustatory stimulus, or a combination thereof.

14. The device of claim 1, wherein the at least one stimulus comprises vibratory and pressure stimuli applied to the outside surface of the subject's neck.

15. The device of claim 1, further comprising:
    one or more physiological sensors electrically coupled to the vibrotactile stimulator;
    a swallowing receptor comprising a piezoelectric sensor;
    a battery, contained within the vibrotactile stimulator, acting as a power supply for the device; and
    a control box configured to select one or more of the stimulus mode, stimulus type, stimulus rate, and stimulus amplitude.

16. The device of claim 1, wherein the vibrotactile stimulator comprises at least one motor or pump.

17. The device of claim 15, wherein the one or more physiological sensors are selected from the group consisting of movement sensors, temperature sensors, skin color sensors, hematocrit sensors, oxygenation sensors, and blood pressure sensors.

18. The device of claim 15, wherein the piezoelectric sensor is configured to be positioned on the outside surface of the subject's skin substantially above the larynx.

19. The device of claim 1, wherein the vibrotactile stimulator comprises:
    a digital clock generator configured to produce an initial clock signal having a first frequency range;
    a digital decade counter configured to receive the initial clock signal and producing sequential pulses having a second frequency range; and
    a motor responsive to the sequential pulses configured to produce vibrations on the subject's larynx, having a third frequency range.

20. The device of claim 19, wherein the initial clock signal is adjustable and comprises a frequency of about one signal every 3 minutes to about one signal every 30 minutes.

21. The device of claim 19, wherein the second frequency range for pulse stimulation is about 1 Hz to about 10 Hz, about 20 Hz to about 75 Hz, or about 30 Hz to about 60 Hz.

22. The device of claim 19, wherein the third frequency range is about 15 Hz to about 200 Hz or about 20 Hz to about 100 Hz.

23. The device of claim 19, wherein the motor comprises a planetary gearbox.

24. The device of claim 19, wherein the motor produces vibrations at a frequency of about 59 Hz.

25. The device of claim 1, wherein the vibrotactile stimulator is configured to apply pressure of about 1 psi to about 14 psi to the subject's neck.

26. The device of claim 5, wherein the automatic timer comprises:
   an automatic clock to initiate onset of the automatic stimulation module;
   an adjustable clock to initiate pulsed stimulation at an adjustable interval of about 0.5 s to about 30 minutes; and
   an adjustable timer configured to set a duration of pulsed stimulation of about 0.1 s to about 500 ms.

27. A method for inducing a swallowing reflex in a subject to prevent drooling and/or aspiration of the subject's own secretions, comprising:
   applying the device to the outside surface of the subject's neck substantially over the subject's larynx, the device comprising:
      a vibrotactile stimulator configured to apply at least one stimulus to the outside surface of a subject's neck, wherein the vibrotactile stimulator comprises:
         a vibrational transducer;
         a manual stimulation module configured to manually engage vibrational transducer;
         an automatic stimulation module configured to automatically engage the vibrational transducer;
         a manual counter configured to determine the number of times the manual stimulation module is engaged; and
         an automatic counter configured to determine the number of times the automatic stimulation module is engaged;
      a connector configured to attach the vibrotactile stimulator to an outside surface of the subject's neck; and
      a switch control communicatively connected to the vibrotactile stimulator and configured to selectively engage the manual stimulation module or the automatic stimulation module; and
   configuring an automatic timer to activate the vibrotactile stimulator about once every 3 minutes to about once every 30 minutes for a duration of about 10 ms to about 20 during which pulsed stimulation is produced at vibrations of about 1 Hz to 300 Hz lasting about 200 ms to about 10 s to induce the swallowing reflex, wherein activating the vibrotactile stimulator includes pulsing the vibrotactile stimulator at a particular rate and for a particular interval to produce the vibrations and applying pressure at about 1 psi to about 14 psi to the subject's neck during an onset period.

28. The method of claim 27, wherein the onset period comprises about 10 ms to about 1.5 s, about 50 ms to about 750 ms, or about 100 ms to about 500 ms.

29. The method of claim 27, wherein the automatic timer is configured to activate the vibrotactile stimulator at an interval of about 1 minute to about 30 minutes.

30. The method of claim 27, wherein the vibrations are at a frequency of about 40 Hz to about 70 Hz.

31. A method for identifying a subject at risk of aspiration from their own secretions, comprising:
   applying a device to an outside surface of the subject's neck substantially over the subject's larynx, the device comprising:
      a vibrotactile stimulator configured to apply at least one stimulus to the outside surface of a subject's neck, wherein the vibrotactile stimulator comprises:
         a vibrational transducer;
         a manual stimulation module configured to manually ngaage the vibrational transducer;
         an automatic stimulation module configured to automatically engage the vibrational transducer;
         a manual counter configured to determine the number of times the manual stimulation module is engaged; and
         an automatic counter configured to determine the number of times the automatic stimulation module is engaged;
      a connector configured to attach the vibrotactile stimulator to an outside surface of the subject's neck;
      a switch control communicatively connected to the vibrotactile stimulator and configured to selectively engage the manual stimulation module or the automatic stimulation module; and
      an actuator, wherein the subject activated the device with the actuator to induce swallowing;
   downloading data from the vibrotactile stimulator after a period of use of the device by the subject; and
   analyzing the data to determine if the subject is at risk of aspiration from their own secretions.

32. The method of claim 31, wherein the secretions are saliva.

33. The method of claim 31, wherein the actuator comprises a button.

34. A method for monitoring subject compliance with a training or therapy regime, comprising:
   applying a device to an outside surface of the subject's neck substantially over the subject's larynx, the device comprising:
      a vibrotactile stimulator configured to apply at least one stimulus to the outside surface of a subject's neck, wherein the vibrotactile stimulator comprises:
         a vibrational transducer;
         a manual stimulation module configured to manually engage the vibrational transducer;
         an automatic stimulation module configured to automatically engage the vibrational transducer;
         a manual counter configured to determine the number of times the manual stimulation module is engaged; and
         an automatic counter configured to determine the number of times the automatic stimulation module is engaged;
      a connector configured to attach the vibrotactile stimulator to an outside surface of the subject's neck;
      a switch control communicatively connected to the vibrotactile stimulator and configured to selectively engage the manual stimulation module or the automatic stimulation module; and
      an actuator, wherein the subject activated the device with the actuator to induce swallowing;
   downloading data from the vibrotactile stimulator after a period of use of the device by the subject; and
   analyzing the data to determine the subject's compliance with the training or therapy regime.

35. The method of claim 34, wherein the subject manually activated or automatically activated the device with the actuator.

36. The method of claim 34, wherein the actuator comprises a button.

* * * * *

UNITED STATES PATENT AND TRADEMARK OFFICE
CERTIFICATE OF CORRECTION

| | | |
|---|---|---|
| PATENT NO. | : 8,388,561 B2 | |
| APPLICATION NO. | : 12/211633 | |
| DATED | : March 5, 2013 | |
| INVENTOR(S) | : Christy Ludlow et al. | |

It is certified that error appears in the above-identified patent and that said Letters Patent is hereby corrected as shown below:

At Title Page 1, Column 2, Item 56, Line 15, Under Other Publications, change "/U82006/" to --/US2006/--.

At Title Page 2, Column 1, Item 56, Line 53, Under Other Publications, change "Seaching" to --Searching--.

At Title Page 3, Column 1, Item 56, Line 13, Under Other Publications, change "dyspagia" to --dysphagia--.

At Title Page 3, Column 2, Item 56, Line 2, Under Other Publications, change "709-716" to --16:709-716--.

In the Specification

In Column 6, Lines 25-26, change "stemothyroid" to --sternothyroid--.

In Column 13, Line 23, change "stemohyoid" to --sternohyoid--.

In Column 14, Line 39, change "thereof" to --thereof.--.

In Column 16, Line 39, change "0.25," to --0.25--.

In Column 17, Line 52, change "stemothyroid" to --sternothyroid--.

In Column 19, Line 32, change "Chatbum," to --Chatburn,--.

In Column 20, Line 2, change "stemum." to --sternum.--.

In Column 20, Line 5, change "stemothyroid" to --sternothyroid--.

In Column 20, Line 6, change "stemohyroid" to --sternohyroid--.

In Column 20, Lines 7-8, change "stemothyroid" to --sternothyroid--.

In Column 24, Line 16, change "(f==2.523," to --(f=-2.523,--.

Signed and Sealed this
Twenty-sixth Day of November, 2013

Margaret A. Focarino
*Commissioner for Patents of the United States Patent and Trademark Office*

CERTIFICATE OF CORRECTION (continued)
U.S. Pat. No. 8,388,561 B2

In the Claims

In Column 35, Line 28, in Claim 27, after "engage" insert --the--.

In Column 35, Line 44, in Claim 27, change "20" to --20 s--.

In Column 36, Line 6, in Claim 31, change "ngaage" to --engage--.